United States Patent [19]

Duggan et al.

[11] Patent Number: 5,098,931

[45] Date of Patent: Mar. 24, 1992

[54] 7-SUBSTITUTED HMG-COA REDUCTASE INHIBITORS

[75] Inventors: Mark E. Duggan, Wynnewood; Wasyl Halczenko, Hatfield; George D. Hartman, Lansdale, all of Pa.

[73] Assignee: Merck & Co., Inc., Rahway, N.J.

[21] Appl. No.: 587,598

[22] Filed: Sep. 24, 1990

Related U.S. Application Data

[63] Continuation of Ser. No. 401,361, Aug. 31, 1989, abandoned.

[51] Int. Cl.$^5$ .................. A61K 31/365; C07D 309/30
[52] U.S. Cl. ..................... 514/460; 514/83; 514/88; 514/89; 514/91; 514/255; 514/227.8; 514/231.5; 514/422; 514/549; 514/824; 514/320; 544/110; 544/147; 544/58.7; 544/337; 544/374; 546/22; 546/206; 548/112; 548/517; 549/222; 549/264
[58] Field of Search .............. 549/264, 242, 222, 60; 514/159, 160, 824, 88, 89, 91, 83, 255, 320, 227.8, 231.5, 422; 546/22, 206; 548/112, 517; 544/337, 374, 110, 147, 58.7

[56] References Cited

U.S. PATENT DOCUMENTS

| | | | |
|---|---|---|---|
| 4,611,067 | 9/1986 | Volante et al. | 549/292 |
| 4,866,090 | 9/1989 | Hoffman et al. | 549/292 |
| 4,921,974 | 5/1990 | Duggan et al. | 546/206 |
| 4,963,538 | 10/1990 | Duggan et al. | 549/292 |

Primary Examiner—Richard L. Raymond
Assistant Examiner—Mark W. Russell
Attorney, Agent, or Firm—Melvin Winokur; Joseph F. DiPrima

[57] ABSTRACT

Novel HMG-CoA reductase inhibitors are useful as antihypercholesterolemic agents and are represented by structural formulae (I) and (II):

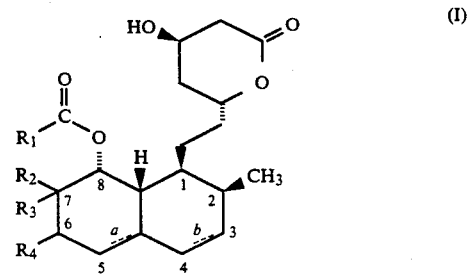

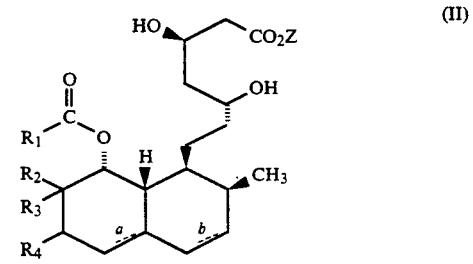

10 Claims, No Drawings

7-SUBSTITUTED HMG-COA REDUCTASE INHIBITORS

This is a continuation of co-pending application Ser. No. 401,361 filed on Aug. 31, 1989 now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihyperchlolesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

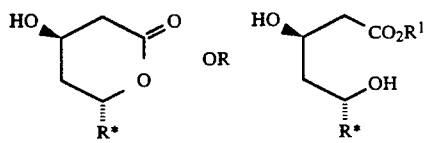

wherein:
$R^1$ is hydrogen, $C_{1-5}$ alkyl or $C_{1-5}$ alkyl substituted with a member of the group consisting of phenyl, dimethylamino, or acetylamino; and
$R^*$ is

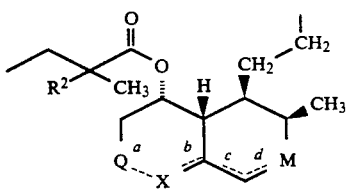

wherein
Q is

or $R^3$—CH; $R^3$ is H or OH; M is

$R^4$ is hydrogen or hydroxy; X is $CR^5R^6$, O, S, or NH; $R^5$ and $R^6$ are H, OH, or $OR^7$ where $R^7$ represents a phosphoryl or acyl moiety;
$R^2$ is hydrogen or methyl; and a, b, c, and d represent single bonds, one of a, b, c or d represents a double bond, or both a and c or both b and d represent double bonds provided that when a is a double bond, Q is

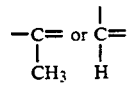

and when d is a double bond, M is

and provided that when $R^5$ or $R^6$ is OH or $OR^7$ or X is O, S, or NH, a, b, and c are single bonds.

U.S. Pat. No. 4,517,373 discloses semi-synthetic hydroxy containing compounds represented by the above general formula wherein $R^*$ is

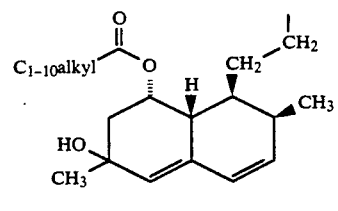

AND

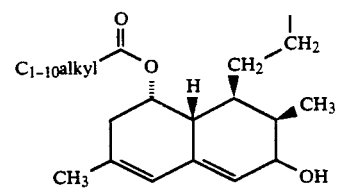

U.S. Pat. No. 4,537,859 and U.S. Pat. No. 4,448,979 also disclose semi-synthetic hydroxy-containing compounds represented by the above general formula wherein $R^*$ is

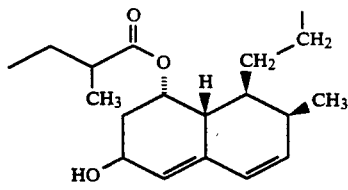

AND

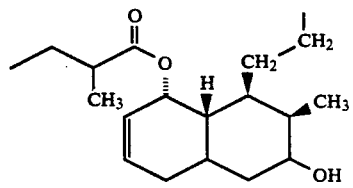

These compounds are prepared by the action of certain microorganisms on the corresponding non-hydroxylated substrates. One such organism described in U.S. Pat. No. 4,537,859 is of the genus Nocardia.

U.K. Patent 2,075,013 discloses semi-synthetic hydroxy containing compounds represented by the above general formula wherein R* is:

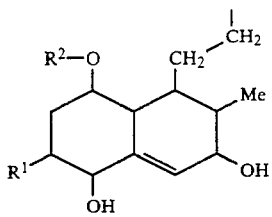

wherein $R^1$ is H or Me, and $R^2$ is H or acyl.

U.S. patent application Ser. No. 254,525 filed Oct. 6, 1988 discloses 6-substituted compounds of the above general formula wherein R* is:

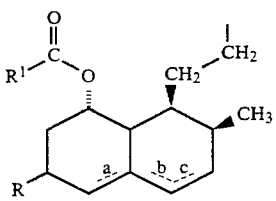

wherein R is $CH_2OH$,

$CH_2OCR^4$, $CO_2R^7$ or $CNR^8R^9$;

and $R^1$, $R^4$, $R^7$, $R^8$ and $R^9$ are broadly defined organic moieties.

U.S. Pat. Nos. 4,604,472 and 4,733,003 disclose compounds of the above formula wherein R* is:

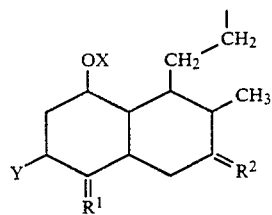

wherein X represents a hydrogen atom or a 2-methylbutyryl group, Y represents a hydrogen atom or a methyl group and $R^1$ and $R^2$ are the same or different and each represents an oxygen atom or a group of formula $=N-OR^3$ where $R^3$ is a hydrogen or alkyl moiety.

Copending U.S. patent application Ser. No. 213,010 filed June 29, 1988 discloses 5-oxygenated compounds of the above general formula wherein R* is

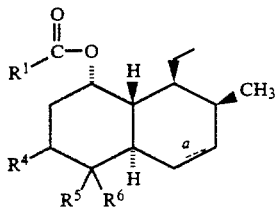

$R^4$ is H, alkyl or substituted alkyl and $R^5$ and $R^6$ are H, OH or $OR^7$ where $R^7$ represents a phosphoryl or acyl moiety.

Copending U.S. patent application Ser. No. 212,767 filed June 29, 1988 discloses 5-Oxa, Thia and Aza compounds of the above general formula where R* is:

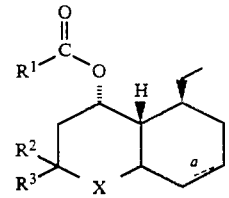

$R^1$ is an alkyl or substituted alkyl group, $R^2$ and $R^3$ are H, alkyl or substituted alkyl and X is O, $S(O)_n$ or $NR^4$ where $R^4$ is H, alkyl or substituted alkyl.

DETAILED DESCRIPTION OF THE INVENTION

This invention relates to HMG-CoA reductase inhibitors of formulae (I) and (II):

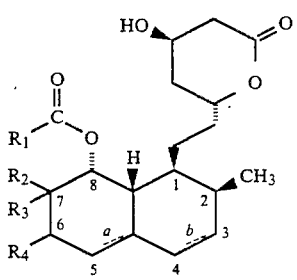

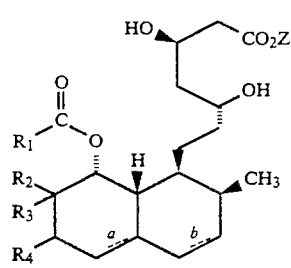

wherein:
$R_1$ is:
(1) $C_{1-10}$ alkyl;
(2) substituted $C_{1-10}$ alkyl in which one or more substituent(s) is selected from:
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$,
 (j) $C_{3-8}$ cycloalkylS(O)$_n$,
 (k) phenylS(O)$_n$,
 (l) substituted phenylS(O)$_n$ in which the substituents are X and Y, and
 (m) oxo;

(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
  (a) $C_{1-10}$ alkyl
  (b) substituted $C_{1-10}$ alkyl in which the substituent is
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from the group consisting of:
  (a) piperidinyl,
  (b) pyrrolidinyl,
  (c) piperazinyl,
  (d) morpholinyl, and
  (e) thiomorpholinyl; and
(17) $R_9S$ in which $R_9$ is selected from
  (a) $C_{1-10}$ alkyl,
  (b) phenyl, and
  (c) substituted phenyl in which the substituents are X and Y;

$R_2$ and $R_3$ are each independently selected from the group consisting of:
(1) H;
(2) OH;
(3) $OR_5$;
wherein;
$R_5$ is

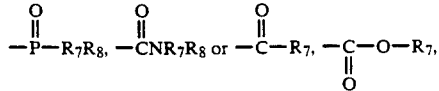

phenyl$C_{1-3}$alkyl, or $C_{1-5}$alkyl;
$R_7$ and $R_8$ independently are H, $C_{1-3}$alkyl, phenyl$C_{1-3}$alkyl wherein aryl is phenyl, naphthyl, pyridyl, furanyl, thienyl; or phenyl, naphthyl, pyridyl, furanyl or thienyl substituted with groups X and Y; provided that when $R_5$ is

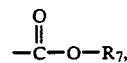

$R_7$ is not H and when $R_5$ is

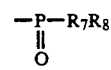

neither $R_7$ nor $R_8$ is H;
(4) $R_6$;
$R_6$ is selected from
(1) $C_{1-10}$ alkyl;
(2) substituted $C_{1-10}$ alkyl in which one or more substituent(s) is selected from:
  (a) halogen,
  (b) hydroxy,
  (c) amino;
  (d) $C_{1-5}$ alkoxy,
  (e) $C_{1-5}$ alkoxycarbonyl,
  (f) $C_{1-5}$ alkylacyloxy,
  (g) phenylacyloxy,
  (h) phenoxycarbonyl,
  (i) phenyl$C_{1-5}$alkylacyloxy,
  (j) phenyl$C_{1-5}$alkoxy,
  (k) $C_{1-5}$alkylamino,
  (l) di($C_{1-5}$alkyl)amino,
  (m) phenylamino,
  (n) substituted phenylamino n which the substituents are X and Y,
  (o) phenyl $C_{1-5}$alkylamino,
  (p) substituted phenyl $C_{1-5}$ alkylamino in which the substituents are X and Y,
  (q) $C_{3-8}$ cycloalkyl,
  (r) phenyl,
  (s) substituted phenyl in which the substituents are X and Y,
  (t) phenylS(O)$_n$,
  (u) substituted phenylS(O)$_n$ in which the substituents are X and Y,
  (v) phenyl-$C_{1-5}$ alkyl-S(O)$_n$,
  (w) $C_{1-5}$ alkylS(O)$_n$,
  (x) phenylaminoacyloxy,
  (y) $C_{1-5}$alkylaminoacyloxy,
  (z) $C_{1-5}$alkylacylamino,
  (aa) di(phenyl$C_{1-5}$alkyl)phosphonyl,
  (bb) di($C_{1-5}$alkyl)phosphinyl,
  (cc) $C_{1-5}$alkyl-carbonyl-,
  (dd) carboxy; or
(3) $R_6$ together with the carbon to which it is attached represents a $C_5$-$C_6$ carbocyclic ring;
provided that when $R_2$ or $R_3$ is OH or $OR_5$, the other is H, alkyl or arylalkyl and provided that both $R_2$ and $R_3$ are not H;

$R_4$ is
(1) hydrogen;
(2) hydroxy;
(3) $C_{1-10}$ alkyl;
(4) substituted $C_{1-10}$ alkyl in which one or more substituents is selected from
 (a) halogen,
 (b) hydroxy,
 (c) $C_{1-10}$ alkoxy,
 (d) $C_{1-5}$ alkoxycarbonyl,
 (e) $C_{1-5}$ alkylacyloxy,
 (f) phenylacyloxy,
 (g) phenoxycarbonyl,
 (h) phenyl $C_{1-5}$ alkylacyloxy,
 (i) phenyl $C_{1-5}$ alkoxy,
 (j) amino,
 (k) $C_{1-5}$ alkylamino,
 (l) di($C_{1-5}$ alkyl)amino,
 (m) phenylamino,
 (n) substituted phenylamino in which the substituents are X and Y,
 (o) phenyl $C_{1-5}$ alkylamino
 (p) substituted phenyl $C_{1-5}$ alkylamino in which the substituents are X and Y,
 (q) $C_{3-8}$ cycloalkyl,
 (r) phenyl,
 (s) substituted phenyl in which the substituents are X and Y,
 (t) phenylS(O)$_n$,
 (u) substituted phenylS(O)$_n$ in which the substituents are X and Y,
 (v) phenyl $C_{1-5}$ alkyl S(O)$_n$,
 (w) $C_{1-5}$ alkylS(O)$_n$,
 (x) phenylaminoacyloxy,
 (y) $C_{1-5}$alkylaminoacyloxy,
 (z) $C_{1-5}$alkylacylamino,
 (aa) di(phenyl$C_{1-5}$alkyl)phosphonyl,
 (bb) di($C_{1-5}$alkyl)phosphinyl,
(5) $R_4$ together with the carbon atom to which it is attached represents a $C_5-C_6$ carbocyclic ring;
X and Y are independently selected from
 a) OH;
 b) halogen,
 c) trifluoromethyl,
 d) $C_{1-3}$alkoxy,
 e) $C_{1-3}$alkylcarbonyloxy,
 f) phenylcarbonyloxy,
 g) $C_{1-3}$alkoxycarbonyl,
 h) phenyloxycarbonyl,
 i) hydrogen,
 j) $C_{1-5}$alkyl;
Z is selected from
 (1) hydrogen;
 (2) $C_{1-5}$alkyl;
 (3) substituted $C_{1-5}$ in which the substituent is selected from
  (a) phenyl,
  (b) dimethylamino, and
  (c) acetylamino, and
 (4) 2,3-dihydroxypropyl; halogen is Cl or F; n is 0, 1 or 2; a and b are double bonds, or one of a and b is a double bond, or both a and b are single bonds; or a pharmaceutically acceptable salt thereof.

Except where specifically defined to the contrary, the terms "alkyl", "alkenyl", "acyl" "aryloxy" and "alkoxy" include both the straight-chain and branched-chain species of the term.

One embodiment of this invention is the class of compounds of formulae (I) and (II) wherein:
$R_1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;
$R_2$ and $R_3$ are each independently selected from the group consisting of:
(1) H;
(2) OH;
(3) OR$_5$;
 wherein;
 R$_5$ is

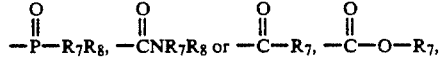

phenyl$C_{1-3}$alkyl, or $C_{1-5}$alkyl;
$R_7$ and $R_8$ independently are H, $C_{1-3}$alkyl, phenyl$C_{1-3}$alkyl or aryl wherein aryl is phenyl, naphthyl, pyridyl, furanyl, thienyl; or phenyl, naphthyl, pyridyl, furanyl or thienyl substituted with groups X and Y; provided that when R$_5$ is

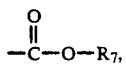

R$_7$ is not H and when R$_5$ is

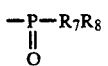

neither R$_7$ nor R$_8$ is H; or
(4) R$_6$;

R$_6$ is selected from
(1) C$_{1-10}$ alkyl;
(2) substituted C$_{1-10}$ alkyl in which one or two substituent(s) is selected from
  (a) halogen,
  (b) hydroxy,
  (c) amino;
  (d) C$_{1-5}$ alkoxy,
  (e) C$_{1-5}$ alkoxycarbonyl,
  (f) C$_{1-5}$ alkylacyloxy,
  (g) phenylacyloxy,
  (h) phenoxycarbonyl,
  (i) phenylC$_{1-5}$alkylacyloxy,
  (j) phenylC$_{1-5}$alkoxy,
  (k) C$_{1-5}$alkylamino,
  (l) di(C$_{1-5}$alkyl)amino,
  (m) phenylamino,
  (n) substituted phenylamino in which the substituents are X and Y,
  (o) phenyl C$_{1-5}$alkylamino,
  (p) substituted phenyl C$_{1-5}$ alkylamino in which the substituents are X and Y,
  (q) C$_{3-8}$ cycloalkyl,
  (r) phenyl,
  (s) substituted phenyl in which the substituents are X and Y,
  (t) phenylS(O)$_n$,
  (u) substituted phenylS(O)$_n$ in which the substituents are X and Y,
  (v) phenyl C$_{1-5}$ alkyl S(O)$_n$,
  (w) C$_{1-5}$ alkylS(O)$_n$,
  (x) phenylaminoacyloxy,
  (y) C$_{1-5}$alkylaminoacyloxy,
  (z) C$_{1-5}$alkylacylamino,
  (aa) di(phenylC$_{1-5}$alkyl)phosphonyl,
  (bb) di(C$_{1-5}$alkyl)phosphinyl,
  (cc) C$_{1-5}$alkyl-carbonyl-,
  (dd) carboxy-; or
(3) R$_6$ together with the carbon to which it is attached represents a C$_{5-6}$ carbocyclic ring;

provided that when R$_2$ or R$_3$ is OH or OR$_5$, the other is H or arylalkyl and provided that both R$_2$ and R$_3$ are not H;

R$_4$ is:
(1) hydrogen;
(2) hydroxy;
(3) C$_{1-10}$ alkyl;
(4) substituted C$_{1-10}$ alkyl in which one or more substituents is selected from:
  (a) halogen,
  (b) hydroxy,
  (c) amino;
(5) CH$_2$R$_{12}$ in which R$_{12}$ is selected from:
  (a) C$_{1-5}$ alkoxy,
  (b) C$_{1-5}$ alkoxy carbonyl,
  (c) C$_{1-5}$ alkylacyloxy,
  (d) phenylacyloxy,
  (e) phenoxycarbonyl,
  (f) phenylC$_{1-5}$alkyl,
  (g) phenylC$_{1-5}$alkoxy
  (h) C$_{1-5}$alkylamino,
  (i) di(C$_{1-5}$alkyl)amino,
  (j) phenylamino,
  (k) substituted phenylamino in which the substituents are X and Y,
  (l) phenyl C$_{1-5}$alkylamino,
  (m) substituted phenyl C$_{1-5}$ alkyl amino in which the substituents are X and Y,
  (n) C$_{3-8}$ cycloalkyl,
  (o) phenyl,
  (p) substituted phenyl in which the substituents are X and Y,
  (q) phenylS(O)$_n$
  (r) substituted phenylS(O)$_n$ in which the substituents are X and Y,
  (s) phenyl C$_{1-5}$ alkylS(O)$_n$,
  (t) C$_{1-5}$ alkylS(O)$_n$,
  (u) phenylaminoacyloxy,
  (v) C$_{1-5}$ alkylaminoacyloxy,
  (w) C$_{1-5}$ alkylacylamino,
  (x) di(phenylC$_{1-5}$alkyl)phosphonyl,
  (y) di(C$_{1-5}$alkyl)phosphinyl;
(6) R$_4$ together with the carbon atom to which it is attached represents a C$_{5-6}$ carbocyclic ring;

X and Y are independently selected from:
  a) OH,
  b) F,
  c) trifluoromethyl,
  d) C$_{1-3}$alkoxy,
  e) hydrogen;
  f) C$_{1-5}$alkyl.

In one class of this embodiment are the compounds of formulae (I) and (II) wherein:
R$_1$ is C$_{1-10}$alkyl;
R$_4$ is H, CH$_3$, CH$_2$OH or OH.

In one subclass are those compounds wherein one of R$_2$ or R$_3$ is H, and the other is:
(a) OH
(b) OR$_5$, or
(c) R$_6$;

Illustrative of this subclass are those compounds of formulae (I) and (II) wherein:
R$_5$ is

C$_{1-5}$alkyl or phenylC$_{1-3}$alkyl;
R$_7$ and R$_8$ are H, C$_{1-3}$alkyl, phenylC$_{1-3}$alkyl or aryl wherein aryl is phenyl or naphthyl or phenyl or naphthyl substituted with X;
R$_6$ is
(a) C$_{1-10}$alkyl;
(b) substituted C$_{1-10}$alkyl in which one or two substituents are selected from:
  (1) hydroxy,
  (2) amino,
  (3) phenyl,
  (4) C$_{1-5}$alkyl-carbonyl-,
  (5) C$_{1-5}$alkyl-acyloxy,
  (6) C$_{1-5}$ alkoxycarbonyl-,
  (7) carboxy.

Further illustrating this subclass are those compounds wherein:
$R_1$ is 2-butyl or 2-methyl-2-butyl;
$R_4$ is $CH_3$.

Exemplifying this subclass are the following compounds:
(1) 6(R)-[2-[8(R)-(2,2-dimethylbutyryloxy)-2(S)-methyl-6(S)-methyl-7(S)-hydroxy-1,2,6,7,8,8a(R)-hexahydronaphthyl-1(S)]ethyl]-4(R)-hydroxy-3,4,5,6-tetrahydro-2H-pyran-2-one;
(2) 6(R)-[2-[8(R)-(2-methylbutyryloxy)-2(S)-methyl-6(S)-methyl-7(S)-hydroxy-1,2,6,7,8,8a(R)-hexahydronaphthyl-1-(S)]ethyl]-4(R)-hydroxy-3,4,5,6-tetrahydro-2H-pyran-2-one;
(3) 6(R)-[2-[8(R)-(2,2-dimethylbutyryloxy)-2(S)-methyl-6(S)-methyl-7(S)-hydroxymethyl-1,2,6,7,8,8a(R)-hexahydronaphthyl-1(S)]ethyl]-4(R)-hydroxy-3,4,5,6-tetrahydro-2H-pyran-2-one;
(4) 6(R)-[2-[8(R)-(2-methylbutyryloxy)-2(S)-methyl-6(S)-methyl-7(S)-hydroxymethyl-1,2,6,7,8,8a(R)-hexahydronaphthyl-1(S)]ethyl]-4(R)-hydroxy-3,4,5,6-tetrahydro-2H-pyran-2-one;
(5) 6(R)-[2-[8(R)-(2,2-dimethylbutyryloxy)-2(S)-methyl-6(S)-methyl-7(R)-methyl-1,2,6,7,8,8a(R)-hexahydronaphthyl-1(S)]ethyl]-4(R)-hydroxy-3,4,5,6-tetrahydro-2H-pyran-2-one;
(6) 6(R)-[2-[8(R)-(2-methylbutyryloxy)-2(S)-methyl-6(S)-methyl-7(R)-methyl-1,2,6,7,8,8a(R)-hexahydronaphthyl-1(S)]ethyl]-4(R)-hydroxy-3,4,5,6-tetrahydro-2H-pyran-2-one;
(7) 6(R)-[2-[8(R)-(2,2-dimethylbutyryloxy)-2(S)-methyl-6(S)-methyl-7(S)-(1(S)-hydroxyethyl)-1,2,6,7,8,8a(R)-hexahydronaphthyl-1(S)]ethyl]-4(R)-hydroxy-3,4,5,6-tetrahydro-2H-pyran-2-one;
(8) 6(R)-[2-[8(R)-(2-methylbutyryloxy)-2(S)-methyl-6(S)-methyl-7(S)-(1(S)-hydroxyethyl)-1,2,6,7,8,8a(R)-hexahydronaphthyl-1(S)]ethyl]-4(R)-hydroxy-3,4,5,6-tetrahydro-2H-pyran-2-one;
(9) 6(R)-[2-[8(R)-(2,2-dimethylbutyryloxy)-2(S)-methyl-6(S)-methyl-7(S)-(1(R)-hydroxyethyl)-1,2,6,7,8,8a(R)-hexahydronaphthyl-1(S)]ethyl]-4(R)-hydroxy-3,4,5,6-tetrahydro-2H-pyran-2-one;
(10) 6(R)-[2-[8(R)-(2-methylbutyryloxy)-2(S)-methyl-6(S)-methyl-7(S)-(1(R)-hydroxyethyl)-1,2,6,7,8,8a(R)-hexahydronaphthyl-1(S)]ethyl]-4(R)-hydroxy-3,4,5,6-tetrahydro-2H-pyran-2-one;
(11) 6(R)-[2-[8(R)-(2,2-dimethylbutylryloxy)-2(S)-methyl-6(S)-methyl-7(S)-(1(S)-hydroxybenzyl)-1,2,6,7,8,8a,(R)-hexahydronaphthyl-1(S)]ethyl]-4(R)-hydroxy-3,4,5,6-tetrahydro-2H-pyran-2-one;
(12) 6(R)-[2-[8(R)-(2-methylbutyryloxy)-2(S)-methyl-6(S)-methyl-7(S)-(1(S)-hydroxybenzyl)-1,2,6,7,8,8a,(R)-hexahydronaphthyl-1(S)]ethyl]-4(R)-hydroxy-3,4,5,6-tetrahydro-2H-pyran-2-one; and the corresponding opened dihydroxy acids and esters.

In a second subclass are those compounds wherein one of $R_2$ or $R_3$ is $R_6$ and the other is OH or $OR_5$.

Illustrative of this subclass are those compounds of formulae (I) and (II) wherein:
$R_5$ is

$C_{1-5}$alkyl or phenyl$C_{1-3}$alkyl;

$R_7$ and $R_8$ are H, $C_{1-3}$alkyl, phenyl$C_{1-3}$alkyl or aryl wherein aryl is phenyl or naphthyl or phenyl or naphthyl substituted with X;
$R_6$ is
(a) $C_{1-10}$alkyl;
(b) substituted $C_{1-10}$alkyl in which one or two substituents are selected from:
 (1) hydroxy,
 (2) amino,
 (3) phenyl,
 (4) $C_{1-5}$alkylcarbonyl-,
 (5) $C_{1-5}$alkylacyloxy-,
 (6) $C_{1-5}$alkoxycarbonyl-,
 (7) carboxy.

Further illustrating this subclass are those compounds wherein:
$R_1$ is 2-butyl or 2-methyl-2-butyl;
$R_4$ is $CH_3$.

The compounds of formula (I) are prepared from lovastatin, mevastatin, pravastatin, or a 6-hydroxymethyl or 8-acyloxy analog thereof following the outline in Schemes 1 through 4.

Scheme 1 outlines a methodology to the 7-hydroxy compounds. The hydroxyl moiety can be converted to any of the $OR_5$ groups following the conversion procedures exemplified in copending U.S. application Ser. No. 322,398 filed Mar. 13, 1989.

Scheme 2 provides a synthetic sequence to the 7-hydroxymethyl analog of formula (I). The hydroxymethyl moiety can be further converted to an iodomethyl moiety by iodination of the hydroxyl (e.g. iodine, triphenylphosphine, imidazole) followed by nucleophilic substitution or radical mediated coupling with an alkyl or heteroatom moiety which results in the elaboration of $CH_2I$ to $R_6$. One example of such methodology is the cross-coupling reaction between an alkyl halide and an organometallic reagent (e.g. alkyliodides with lithium dialkyl copper—Posner Org. React. 22, 253–400 (1975).

Scheme 3 illustrates a route to the 7-alkyl compounds of formula (I). The sequence may be generalized to yield the 7-substituted $R_6$ compounds of formula (I) by substituting $R_6I$ in place of MeI in the sequence (3-4)→(3-5).

Scheme 4 provides a methodology to the 7-(α-hydroxyalkyl) analogs of formula I. The hydroxyalkyl moiety can be further converted to an iodoalkyl moiety by iodination of the hydroxyl (e.g. iodine, triphenylphosphine, imidazole) followed by nucleophilic substitution or radical mediated coupling with an elaboration of alkyl iodide to $R_6$. One example of such methodology is the cross-coupling reaction between an alkyl halide and an organometallic reagent (e.g. alkyliodides with lithium dialkyl copper—Posner Org. React. 22, 253.400 (1975).

Where the acyl moiety of the starting material is other than 2-methylbutyryl the acyl group of lovastatin may be hydrolyzed and the hydroxyl group reesterified with an appropriate alkanoyl halide following the procedure in U.S. Pat. No. 4,444,784. The alkanoyl halide can be formed by standard transformations such as substitution with an alkyl moiety or other appropriate electrophile at an acidic C—H site on an available starting material. Where $R_4$ is 6-hydroxymethyl or a protected hydroxymethyl the conversion of 6-methyl to 6-hydroxymethyl can be accomplished following the procedure in Ser. No. 254,525 filed Oct. 6, 1988; the "525" application also discloses a method of preparing the 6-α-desmethyl-6-β-methyl lovastatin derivative which may be employed as a starting material in the above scheme.

Where the reaction conditions of the above noted chemical transformations would be deleterious to the substituents in the 8-acyloxy moiety, the acetoxy group can be employed as a protecting group which after the elaboration of the 7-position can be removed by hydrolysis to give the 8-hydroxy derivative which then can be acylated according to the general procedures described in U.S. Pat. No. 4,661,483.

SCHEME 1

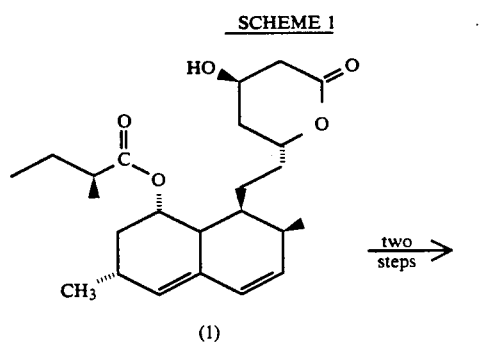

(1)

two steps →

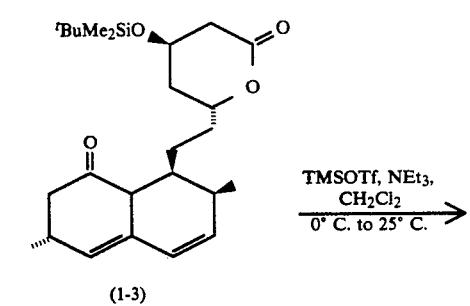

(1-2)

PCC, CH₂Cl₂, 4A sieves →

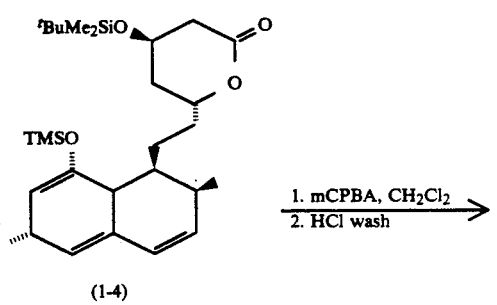

(1-3)

TMSOTf, NEt₃, CH₂Cl₂
0° C. to 25° C. →

(1-4)

1. mCPBA, CH₂Cl₂
2. HCl wash →

-continued
SCHEME 1

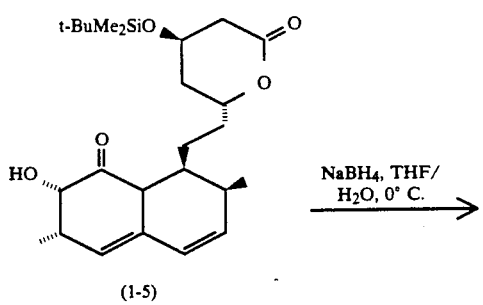

(1-5)

NaBH₄, THF/H₂O, 0° C. →

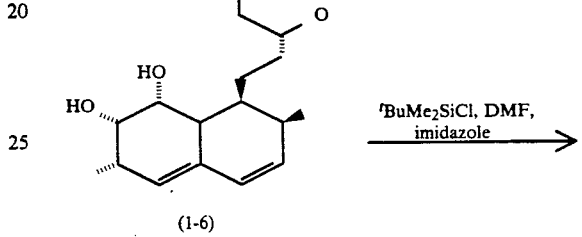

(1-6)

tBuMe₂SiCl, DMF, imidazole →

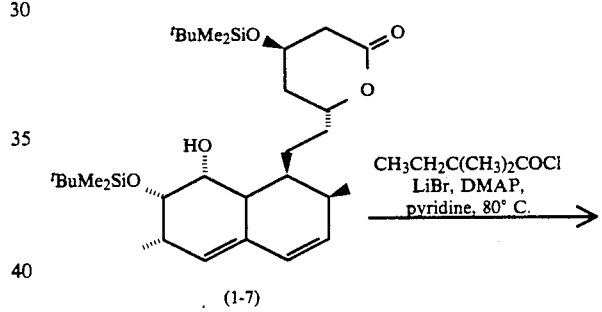

(1-7)

CH₃CH₂C(CH₃)₂COCl
LiBr, DMAP, pyridine, 80° C. →

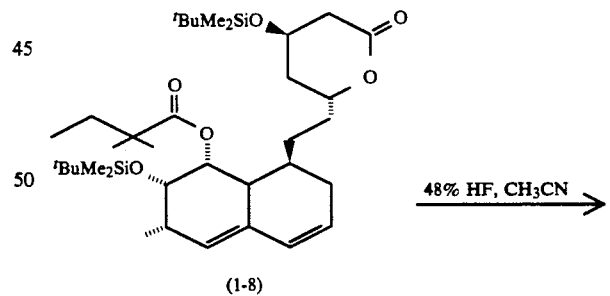

(1-8)

48% HF, CH₃CN →

(1-9)

SCHEME 2
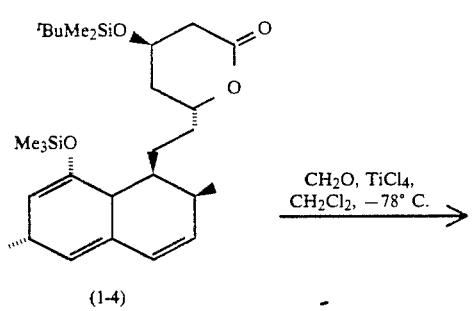
(1-4)
CH₂O, TiCl₄,
CH₂Cl₂, −78° C.
→
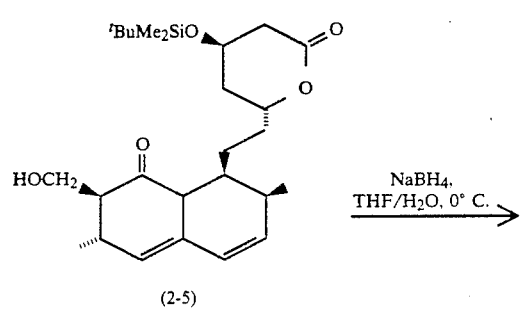
(2-5)
NaBH₄,
THF/H₂O, 0° C.
→
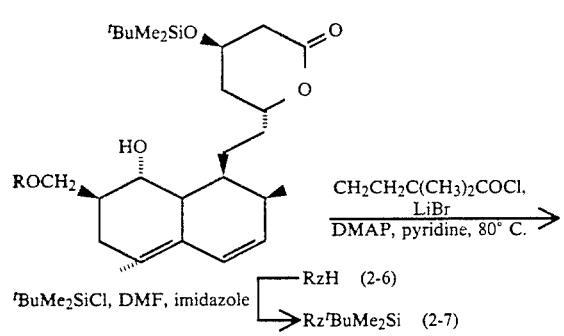
CH₂CH₂C(CH₃)₂COCl,
LiBr
DMAP, pyridine, 80° C.
→
RzH (2-6)
'BuMe₂SiCl, DMF, imidazole
→ Rz'BuMe₂Si (2-7)
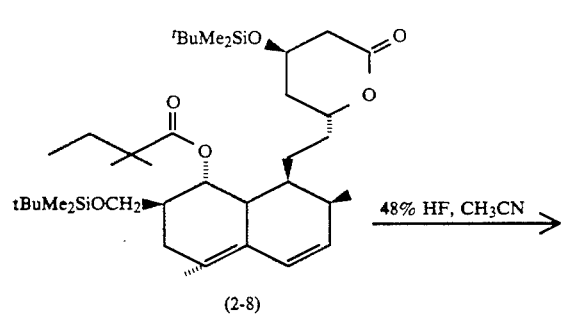
(2-8)
48% HF, CH₃CN
→
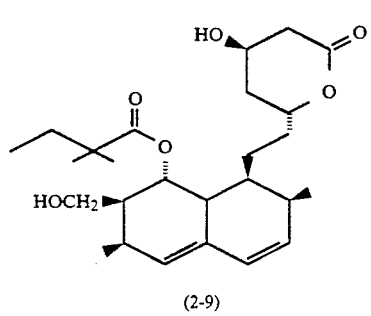
(2-9)
SCHEME 3
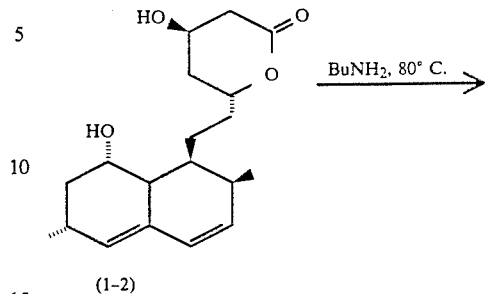
(1-2)
BuNH₂, 80° C.
→
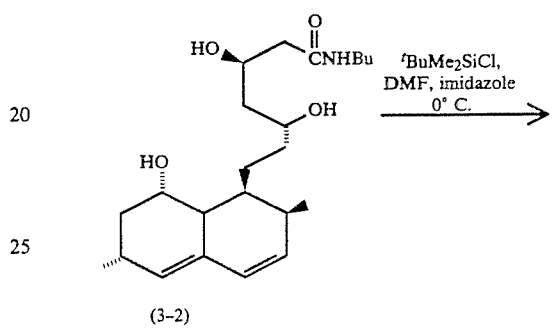
(3-2)
'BuMe₂SiCl,
DMF, imidazole
0° C.
→
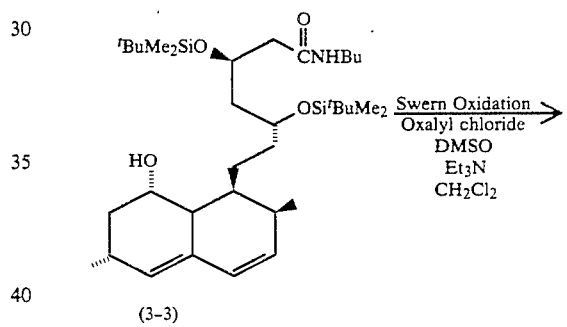
(3-3)
Swern Oxidation
Oxalyl chloride
DMSO
Et₃N
CH₂Cl₂
→
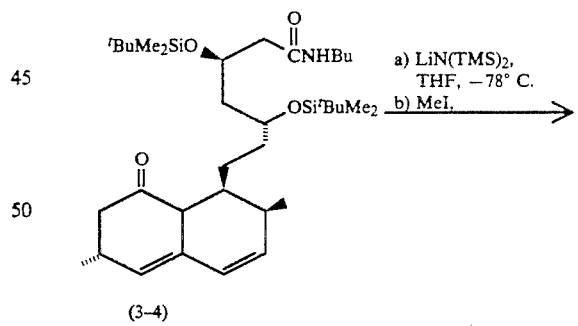
(3-4)
a) LiN(TMS)₂,
THF, −78° C.
b) MeI,
→
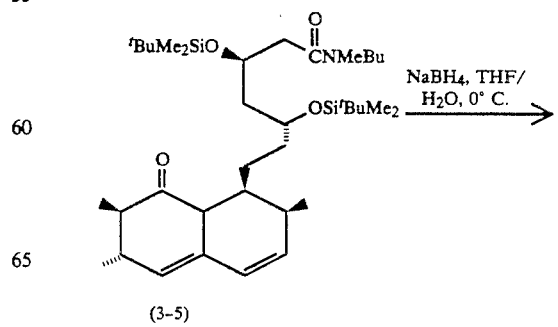
(3-5)
NaBH₄, THF/
H₂O, 0° C.
→

-continued
SCHEME 3
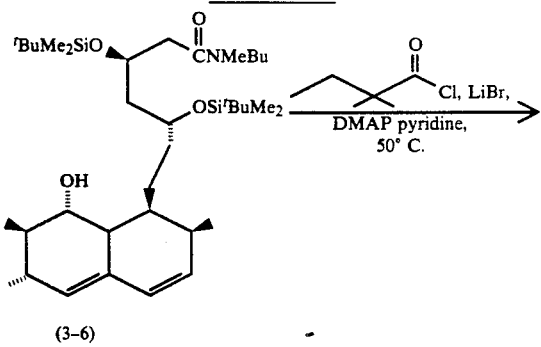
(3-6)
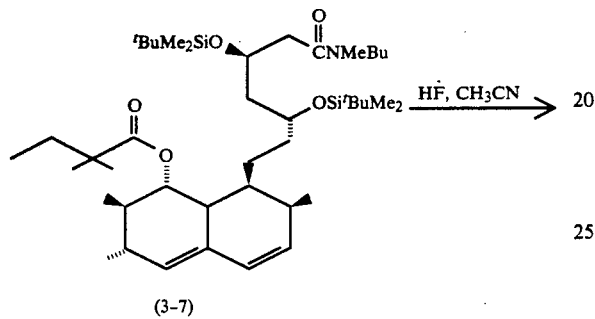
(3-7)
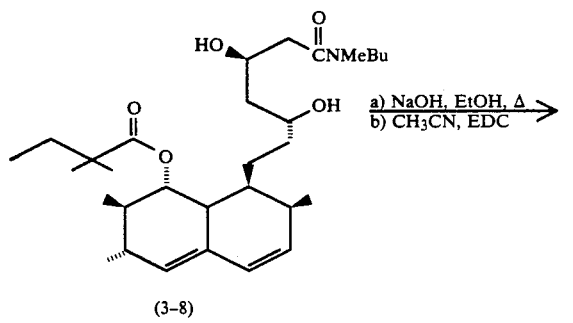
(3-8)
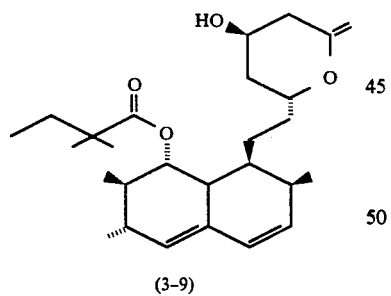
(3-9)
SCHEME 4
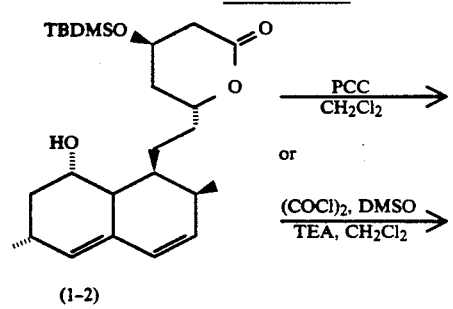
(1-2)
-continued
SCHEME 4
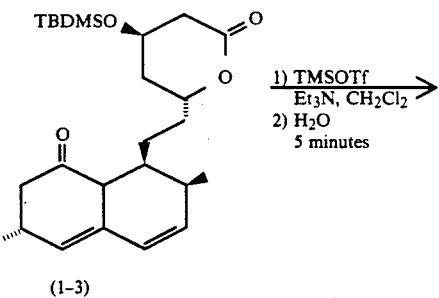
(1-3)
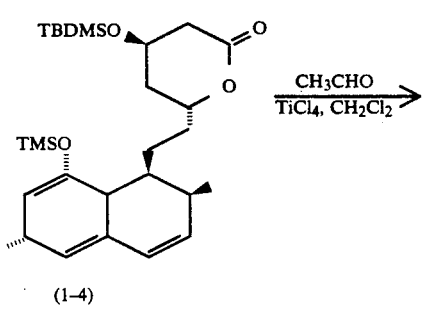
(1-4)
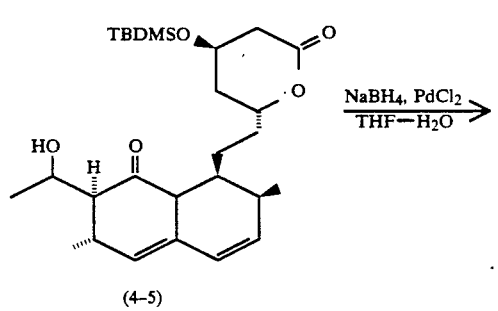
(4-5)
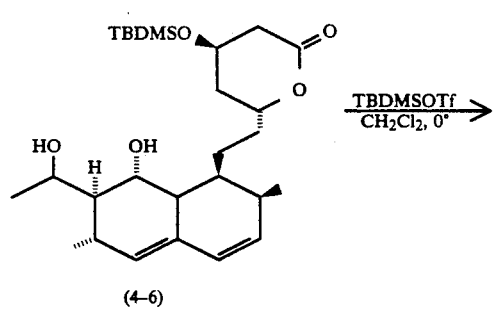
(4-7)

-continued
SCHEME 4

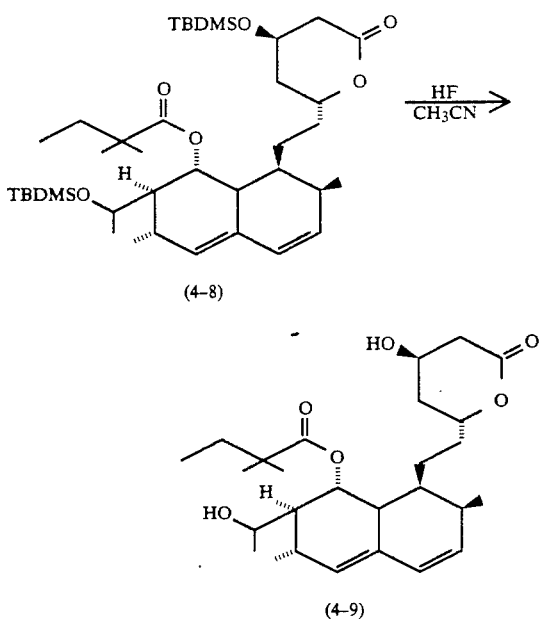

Where the product formed by the above described synthetic pathways is not the desired form of that compound, then that product may be subjected to one or more further reactions such as hydrolysis, disilylation, ammonolysis or lactonization by conventional methods.

Preferred metal salts of the compounds of the present invention are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, a, β-diaminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-$C_{1-5}$alkyl may be employed if desired.

Metal salts of the carboxylic acids of formula (II) may be obtained by contacting a hydroxide, carbonate or similar solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example, a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desire product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347-358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol.

Representative of the intrinsic HMG-CoA reductase inhibitory activities of the claimed compounds are the following relative potencies for compounds of formula (I).

| Compound | Relative Potency (Compactin = 100) |
|---|---|
| 6R-[2-[8(R)-(2,2-dimethyl-butyryloxy)-2(S)-methyl-6(S)-methyl-7(S)-hydroxy-1,2,6,7,8,8a(R)-hexahydro-naphthyl-1(S)]ethyl]-4(R)-hydroxy-3,4,5,6-tetrahydro-2H-pyran-2-one | 214 |
| 6(R)-[2-[8(R)-(2,2-dimethylbutyryloxy)-2(S)-methyl-6(S)methyl-7(S)-hydroxymethyl-1,2,6,7,8,8a(R)-hexahydronaphthyl-1(S)]ethyl]-4(R)-hydroxy-3,4,5,6-tetrahydro-2H-pyran-2-one | 262 |
| 6(R)-[2-[8(R)-(2,2-dimethylbutyryloxy)-2(S)-methyl-6(S)-methyl-7(R)-methyl-1,2,6,7,8,8a(R)-hexahydronaphthyl-1(S)]ethyl]-4(R)-hydroxy-3,4,5,6-tetrahydro-2H-pyran-2-one | 174 |
| 6(R)-[2-[8(R)-(2,2-dimethylbutyryloxy)-2(S)-methyl-6(S)-methyl-7(S)-(1(S)-hydroxyethyl)-1,2,6,7,8,8a(R)-hexahydronaphthyl-1(S)]ethyl]-4(R)-hydroxy-3,4,5,6-tetrahydro-2H-pyran-2-one | 350 |
| 6(R)-[2-[8(R)-(2,2 dimethylbutyryloxy)-2(S)-methyl-6(S)-methyl-7(S)-(1(R)-hydroxyethyl)-1,2,6,7,8,8a(R)-hexahydronaphthyl-1(S)]ethyl]-4(R)-hydroxy-3,4,5,6-tetrahydro-2H-pyran-2-one | 124 |
| 6(R)-[2-[8(R)-(2,2-dimethylbutyryloxy)-2(S)-methyl-6(S)-methyl-7(S)-(1(S)-hydroxybenzyl)-1,2,6,7,8,8a(R)-hexahydronaphthyl-1(S)]ethyl]-4(R)-hydroxy-3,4,5,6-tetrahydro-2H-pyran-2-one | 137 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)imino-trimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto:

EXAMPLE 1

Preparation of 6R-[2-[8(R)-(2,2-dimethylbutyryloxy)-2(S)-methyl-6(S)-methyl-7(S)-hydroxy-1,2,6,7,8,8a(R)-hexahydronaphthyl-1(S)]ethyl]-4(R)-hydroxy-3,4,5,6-tetrahydro-2H-pyran-2-one. (1-9)'

Step A:
6(R)-[2-(8(S)-hydroxy-2(S),6(R)-dimethyl-1,2,6,7,8,8a(R)-hexahydronaphthyl-1(S)-ethyl]-4(R)-hydroxy-3,4,5,6-tetrahydro-2H-pyran-2-one A mixture of 8.0 g (19.78 mmole) of lovastatin and 8.31 g (187.8 mmole) of LiOH.H$_2$O in 600 ml of water was stirred at reflux under a nitrogen atmosphere for 56 hours. The reaction mixture was cooled to 0° and treated, with stirring, with 20 ml of concentrated hydrochloric acid. The mixture was then extracted with three 250 ml portions of ether and the combined extracts were washed successively with three 200 ml portions of water and then 200 ml of saturated brine. After drying over MgSO$_4$, this organic solution was filtered and the solvent evaporated in vacuo to give an oily residue. This residue was dissolved in 200 ml of toluene and heated at reflux under a nitrogen atmosphere for 2 hours with continuous separation of water to effect relactonization. Evaporation of the toluene and trituration of the residue with hexane gave the title compound as a white solid which did not require further purification.

An analytical sample was prepared by recrystallization of a portion of this material from butyl chloride to give white clusters: m.p. 128°–131° (vacuum); NMR(CDCl$_3$) δ0.87(d,J=7 Hz,3H) 1.16 (d,J=7 Hz, 3H), 2.64 (m,2H), 4.27 (brm,1H)4.37 (m,1H), 4.71 (m,1H,), 5.56 (m,1H,), 5.79 (dd, J=6,10 Hz, 1H), 6.03 (d,J=10 Hz, 1H); IR (CHCl$_3$) 3400 (OH), 1725 (C=O), 1240, 1120, 1080 cm$^{-1}$.

Anal. Calcd for C$_{19}$H$_{28}$O$_4$.0.1C$_4$H$_9$Cl C, 70.67; H, 8.84. Found: C, 70.77; H, 8.75.

Step B: Preparation of 6(R)-[2-[8(S)-hydroxy-2(S),6(R)-dimethyl-1,2,6,7,8,8a(R)-hexahydronaphthyl-1(S)ethyl]-4(R)-(dimethyltertbutylsilyoxy)-3,4,5,6-tetrahydro-2H-pyran-2-one. (1-2)'

A mixture of the alcohol from Step A (18.3 g, 57.1 mmol), 21.5 g (142.8 mmol) of tert-butyldimethylchlorosilane and 19.4 g (285.6 mmol) of imidazole in 200 ml of N,N-dimethylformamide was stirred at 20° under a nitrogen atmosphere for 18 hours. The reaction mixture was then diluted with 1500 ml of ether and washed successively with water, 2% aqueous hydrochloric acid, water and saturated sodium bicarbonate. The ether solution was dried over MgSO$_4$, filtered and reduced to a volume of 1 L. After addition of 600 ml of hexane, the volume was reduced to 600 ml on a steam bath. The product crystallized at room temperature; after isolation and air drying this provided a white cottony solid. The mother liquors were reduced to 250 ml and a second crop of crystals was isolated after this solution stood at 0° overnight. m.p. 142°-144° (vac); NMR(CDCl₃) δ0.10 (s,6H,) 0.90 (s,9H), 1.19 (d,J=7 Hz, 3H), 2.58 (d,J=4 Hz, 2H), 4.3 (m,2H) 4.70 (m,1H,), 5.57 (m,1H,), 5.58 (dd,J=6,10 Hz,1H), 6.03 (d,J=10 Hz,1H).

Anal. Calcd for C₂₅H₄₂O₄Si: C, 69.08, H, 9.74. Found: C, 69.46; H, 9.83.

Step C: Preparation of 6(R)-[2-[8-oxo-2(S)-methyl-6(R)-methyl-1,2,6,7,8,8a(R)-hexahydronaphthyl-1(S)]ethyl]-4(R)-tert-butyldimethylsilyloxy-3,4,5,6-tetrahydro-2H-pyran-2-one (1-3)'

To a stirred mixture of alcohol (1-2)' (15.0 g, 34 mmol), crushed 4Å sieves (~5.0 g), and CH₂Cl₂ (185 mL) at 0° C. was added PCC (23.9 g, 0.11 mol). After 5 minutes the cooling bath was removed and the reaction was stirred for an additional 30 minutes. The reaction mixture was diluted with ether, filtered through a pad of silica, and the filtrate concentrated. Flash chromatography (silica, 15% to 20% ethyl acetate/hexanes) gave (1-3)' as a crystalline solid.

TLC (silica) Rf=0.50 (30% ethyl acetate/hexanes); ¹H NMR (CDCl₃) δ5.97 (d,J-9.98 Hz, 1H), 5.76 (dd,J=9.8 and 5.9 Hz, 1H), 5.47 (bs,1H), 4.59 (m,1H), 4.23 (m,1H), 2.80 (m,2H), 2.55 (m,3H), 2.35 (m,1H), 2.03 (dd,J=14 and 9 Hz,1H), 1.95–1.4 (m), 1.07 (d,J=7 Hz,3H), 0.87 (d,J=7 Hz,3H), 0.83 (s,9H), 0.03 (s,6H).

Step D: Preparation of 6(R)-[2-[8-trimethylsilyloxy-2(S)-methyl-6(S)-methyl-1,2,6,8a(R)-tetrahydronaphthyl-1(S)]ethyl]-4(R)-tert-butyldimethylsilyloxy-3,4,5,6-tetrahydro-2H-pyran-2-one (1-4)'

To a stirred solution of ketone (1-3)' (24 g, 59 mmol), triethylamine(41.1 mL, 0.29 mol), and CH₂Cl₂ (300 mL) at 0° C. was added trimethylsilytriflate (22.9 mL, 0.12 mol) portionwise over a 5 minute period. After 30 minutes the cooling bath was removed and H₂O (50 mL) was added to the reaction mixture. After stirring for 5 minutes the reaction mixture was diluted with ether, washed with H₂O and brine, dried (MgSO₄), and concentrated. Flash chromatography (silica, 12% ethyl acetate/hexanes) gave (1-4)' as a colorless oil.

TLC Rf=0.46 (20% ethyl acetate/hexanes); ¹H NMR (CDCl₃) 5.99(d,J=10 Hz,1H), 5.61(dd,J=10 and 5 Hz,1H), 5.32(m,1H), 4.84(dd,J=4 and 1 Hz,1H), 4.62(m,1H), 4.27(m,1H), 2.90(m,1H), 2.63-2.52(m,3H), 2.30(m,1H), 1.95-1.45(m), 1.01(d,J=7 Hz,3H), 0.91(d,J=7 Hz,3H), 0.85(S,9H), 0.16(S,9H), 0.04(S,3H), 0.03(S,3H).

Step E: Preparation of 6(R)-[2-[8-oxo-2(S)-methyl-6(S)-methyl-7(S)-hydroxy-1,2,6,7,8a(R)-pentahydronaphthyl-1(S)]ethyl]-4(R)-tert-butyldimethylsilyloxy-3,4,5,6-tetra-2H-pyran-2-one (1-5)'

To a stirred solution of silyl enol ether (1-4)' (25.0 g, 49 mmol) and ethyl acetate (500 mL) at 0° C. was added 55% m-CPBA(17.1 g, 54 mmol). After 30 minutes 10% Na₂SO₃ (250 mL) was added to the reaction mixture, followed by continued stirring for 5 minutes. The phases were separated and the organic portion was washed with 1N HCl, H₂O, and brine, dried (MgSO₄), and concentrated. Flash chromatography (silica, 12% ethyl acetate/hexanes) gave alcohol (1-5)' as colorless crystals.

TLC Rf=0.46 (20% ethyl acetate/hexanes); ¹H NMR(CDCl₃) δ5.98(d,J=10 Hz,1H), 5.61(dd,J=10 and 5 Hz,1H), 5.49(m,1H), 4.69(dd,J=6 and 6 Hz,1H), 4.62(m,1H), 4.27(m,1H), 3.28(bd,J=11 Hz,1H) 3.16(m,1H), 2.58(m,2H), 2.38(m,1H), 2.2-1.3(m), 0.91(d,J=7 Hz,3H), 0.88(S,9H), 0.83(d,J=7 Hz,3H) 0.04(S,6H).

Step F: Preparation of 6(R)-[2-[8(R)-hydroxy-2(S)-methyl-6(S)-methyl-7(S)-hydroxy-1,2,6,7,8,8a(R)-hexahydronaphthyl-1(S)]ethyl]-4(R)-tert-butyldimethylsilyloxy-3,4,5,6-tetrahydro-2H-pyran-2-one (1-6)'

To a stirred solution of ketone (1-5)' (20.0 g, 45 mmol), THF (400 mL), and H₂O (45 mL) at 0° C. was added NaBH₄ (5.1 g, 0.13 mol) in two portions. After 45 minutes the reaction mixture was diluted with ether, washed with H₂O and brine, dried (MgSO₄), and concentrated. Flash chromatography (silica, 40% ethyl acetate/hexanes) gave diol (1-6)' as a colorless oil.

TLC Rf=0.69 (ethyl acetate); ¹H NMR (CDCl₃) δ5.99(d,J=10 Hz,1H), 5.8(dd,J=10 and 5 Hz, 1H), 5.51(m,1H), 4.69(m,1H), 4.3(m,1H), 4.16(m,1H), 3.90(ddd,J=7,7 and 2 Hz,1H), 2.69(m,1H), 2.60(m,2H), 2.39(m,1H), 2.3(d,7 Hz,1H), 2.27(m,1H), 1.95-1.4(m), 1.16(d,J=7 Hz,3H), 0.88(d,J=7 Hz,3H), 0.86(S,9H), 0.06(S,3H), 0.05(S,3H).

Step G: Preparation of 6(R)-[2-[8(R)-hydroxy-2(S)-methyl-6(S)-methyl-7(S)-tert-butyldimethylsilyloxy-1,2,6,7,8,8a(R)-hexahydronaphthyl-1(S)]ethyl]-4(R)-tert-butylidimethylsilyloxy-3,4,5,6-tetrahydro-2H-pyran-2-one (1-7)'

To a stirred solution of diol (1-6) (5.8 g, 13 mmol), imidazole (1.8 g, 27 mmol), and DMF (43 mL) at 0° C. was added tert-butyldimethylsilyl chloride (2.0 g, 14 mmol). After 30 minutes the cooling bath was removed and stirring was continued overnight. After 20 hours the reaction mixture was diluted with hexane, washed with H₂O (2×) and brine, dried (MgSO₄), and concentrated. Flash chromatography (silica, 15% ethyl acetate/hexanes) gave (1-7)' as a colorless oil.

TLC Rf=0.69 (30% ethyl acetate/hexanes); ¹H NMR (CHCl₃) δ5.99(d,J=10 Hz,1H), 5.79(dd,J=10 and 5 Hz,1H), 5.5(m,1H), 4.65(m,1H), 4.28(m,1H), 4.0(bs,1H), 3.9(m,1H), 2.6(m,2H), 2.5(m,1H), 2.37(m,1H), 2.24(m,1H), 2.00-1.4(m), 1.16(d,J=7 Hz,3H), 0.92(S,9H), 0.9(d,J=7 Hz,3H), 0.86(S,9H), 0.08(S,6H), 0.04(S,6H).

Step H: Preparation of 6(R)-[2-[8(R)-(2,2-dimethylbutyryloxy)-2(S)-methyl-6(S)-methyl-7(S)-tert-butyl-dimethylsilyloxy-1,2,6,7,8,8a(R)hexahydronaphthyl-1(S)]ethyl]-4(R)-tert-butyldimethylsilyloxy-3,4,5,6-tetrahydro-2H-pyran-2-one (1-7)'

To a stirred mixture of alcohol (1-7)' (0.94 g, 1.6 mmol), anhydrous LiBr(0.72 g, 8.3 mmol; dried at 125° C. for 16 hours at 0.05 mmHg), 4-dimethylaminopyridine (30 mg, 0.2 mmol), and pyridine (2.0 mL) at 25° C. was added 2,2-dimethylbutyryl chloride (0.57 mL, 4.1 mmol) followed by heating at 80° C. for 3.0 hours. The cooled reaction mixture was diluted with ether, washed with H₂O and brine, dried (MgSO₄), and concentrated. Flash chromatography (silica, 10% ethyl acetate/hexanes) gave ester (1-8)' as an oil.

TLC Rf=0.42 (20% ethyl acetate/hexanes); ¹H NMR (CDCl₃) δ5.99(d,J=10 Hz,1H), 5.78(dd,J=10 and 5 Hz,1H), 5.53(m,1H), 4.60(m,1H), 4.29(m,1H), 4.03(dd,J=7 and 2 Hz,1H), 2.7–2.3(m), 2.0–1.2(m), 1.14(d,J=7 Hz,3H), 1.13(S,3H), 1.12(S,3H), 0.93(d,J=7 Hz,3H), 0.9(S,18H), 0.89(t,J=7 Hz,3H), 0.1(S,9H), 0.1(S,3H).

Step I: Preparation of 6(R)-[2-[8(R)-(2,2-dimethylbutyryloxy)-2(S)-methyl-6(S)-methyl-7(S)-hydroxy-1,2,6,7,8,8a(R)-hexahydronaphthyl-1(S)]ethyl]-4(R)-hydroxy-3,4,5,6-tetrahydro-2H-pyran-2-one (1-9)'

To a vigorously stirred solution of bis-silyl ether (1-8)' (4.7 g, 7.1 mmol) and acetonitrile (70 mL), in a plastic container, at 25° C. was added 48% HF (30 mL, 71 mmol). After 30 minutes additional 48% HF (5.0 mL) was added. After 30 minutes the reaction mixture was carefully poured into a vigorously stirred mixture of sat. NaHCO₃ and ether. After gas evolution subsided the organic portion was washed with H₂O (2×) and brine, dried (MgSO₄), and concentrated. Flash chromatography (silica, 70% ethyl acetate/hexanes) gave diol (1-9)' as a foam. The product (1-9)' was crystallized from ethyl acetate/hexanes to give a colorless powder mp=138°–139° C.

TLC Rf=0.15 (ethyl acetate); ¹H NMR (CDCl₃) δ6.03(d,J=10 Hz,1H), 5.82(dd,J=10 and 6 Hz,1H), 5.68(m,1H), 5.47(m,1H), 4.65(m,1H), 4.42(m,1H), 4.17(m,1H), 3.06(d,J=4 Hz,1H), 2.77(dd,J=17 and 5 Hz,1H), 2.70(m,1H), 2.67(m,1H), 2.49(m,1H), 2.40(m,1H), 2.05–1.27(m), 1.19(S,3H), 1.18(S,3H), 1.12(d,J=7 Hz,3H), 0.92(d,J=7 Hz,3H), 0.89(S,3H).

EXAMPLE 2

Preparation of 6(R)-[2-[8(R)-(2,2-dimethylbutyryloxy)-2(S)-methyl-6(S)-methyl-7(S)-hydroxymethyl-1,2,6,7,8,8a(R)-hexahydronaphthyl-1(S)]ethyl]-4(R)-hydroxy-3,4,5,6-tetra-2H-pyran-2-one (2-9)'

Step A: Preparation of 6(R)-[2-[8-oxo-2(S)-methyl-6(S)-methyl-7(S)-hydroxymethyl-1,2,6,7,8a(R)-pentahydronaphthyl-1(S)]ethyl]-4(R)-tert-butyldimethylsilyloxy-3,4,5,6-tetra-2H-pyran-2-one (2-5)'

To a stirred solution of silyl enol ether (1-4)' (26.0 g, 51 mmol) in CH₂Cl₂ (550 mL) at −78° C. was bubbled formaldehyde gas by heating a flask containing paraformaldehyde (20 g) and phosphorus pentoxide (5 g) gently with a bunsen burner until gas evolution ceased. TiCl₄ (6.2 mL, 56 mmol) was then added dropwise to effect an orange heterogeneous mixture. After addition was complete the reaction mixture was stirred for 45 minutes at −78° C. The cold solution was poured carefully into a stirred mixture of ether and saturated NaHCO₃. The organic portion was washed with H₂O and brine, dried (MgSO₄), and concentrated. Flash chromatography (silica, 30% ethyl acetate/hexanes) afforded the ketone (2-5)' as a colorless oil.

TLC Rf=0.16 (30% ethyl acetate/hexanes); ¹H NMR (CDCl₃) δ5.98 (d, J=10 Hz, 1H), 5.72 (dd, J=10 and 6 Hz, 1H), 5.42 (bs, 2H), 4.57 (m, 1H), 4.23 (m, 1H), 3.85 (m, 1H), 3.77 (m, 1H), 2.73 (bd, J=11 Hz, 1H), 2.53 (m, 3H), 2.35 (m, 1H), 2.20 (m, 1H), 2.0–1.35 (m), 1.13 (d, J=7 Hz, 3H), 0.88 (d, J=7 Hz, 3H), 0.83 (s, 9H), 0.02 (s, 6H).

Step B: Preparation of 6(R)-[2-[8(R)-hydroxy-2(S)-methyl-6(S)-methyl-7(S)-hydroxymethyl-1,2,6,7,8,8a(R)-hexahydronaphthyl-1(S)]ethyl]-4(R)-tert-butyldimethylsilyloxy-3,4,5,6-tetrahydro-2H-pyran-2-one (2-6)'

To a stirred solution of ketone (2-5)' (30 g, 65 mmol), THF (1.2 L), and H₂O (120 mL) at 0° C. was added NaBH₄ (12.2 g, 0.32 mol) in 5 portions over a 3.0 hour period. The reaction mixture was diluted with ether, washed with H₂O (2×) and brine, dried (MgSO₄), and concentrated. Flash chromatography (silica, 45% ethyl acetate/hexanes) gave diol (2-6) (26 g) as a solid. Recrystallization (ethyl acetate/hexanes) gave (2-6)' as fine needles. mp=148°–149° C.; TLC Rf=0.33 (50% ethyl acetate/hexanes); ¹H NMR (CDCl₃) 5.99 (d, J=10 Hz, 1H), 5.82 (dd, J=10 and 6 Hz, 1H), 5.5 (m, 1H), 4.70 (m, 1H), 4.31 (m, 1H), 3.54 (m, 2H), 2.60 (m, 2H), 2.39 (m, 1H), 2.25–1.45 (m), 1.25 (d, J=7 Hz, 3H), 0.93 (d, J=7 Hz, 3H), 0.91 (s, 9H), 0.02 (s, 3H).

Step C: Preparation of 6(R)-[2-[8(R)-hydroxy-2(S)-methyl-6(S)-methyl-7(S)-tert-butyldimethylsilyloxymethyl-1,2,6,7,8,8a(R)-hexahydronaphthyl-1(S)]ethyl]-4(R)-tert-butyldimethylsilyloxy-3,4,5,6-tetrahydro-2H-pyran-2-one (2-7)'

To a stirred solution of diol (2-6)' (2.8 g, 6.0 mmol), imidazole (0.9 g, 13.2 mmol), and dry DMF (5.0 mL) at 0° C. was added tert-butyldimethylsilyl chloride (1.0 g, 6.3 mmol) in one portion. After 2.0 hours the reaction mixture was diluted with hexanes, washed with H₂O (2×) and brine, dried (MgSO₄), and concentrated to furnish a crystalline solid. Recrystallization (ethyl acetate/hexanes) gave (2-7)' as colorless crystals.

m.p.=108°–109° C.; TLC Rf=0.26 (20% ethyl acetate/hexanes); ¹H NMR (CDCl₃) 5.99 (d, J=10 Hz, 1H), 5.82 (dd, J=10 and 6 Hz, 1H), 5.50 (bs, 1H), 4.69 (m, 1H), 4.29 (m, 2H), 3.47 (m, 2H) 2.6 (m, 2H), 2.4 (m, 1H), 2.2–1.4 (m), 1.35 (d, J=9 Hz, 1H), 1.21 (d, J=7 Hz, 3H) 0.92 (d, J=7 Hz, 3H), 0.9 (s, 18H), 0.1 (s, 3H) 0.09 (s, 3H), 0.06 (s, 6H).

Step D: Preparation of 6(R)-[2-[8(R)-(2,2-dimethylbutyryloxy)-2(S)-methyl-6(S)-methyl-7(S)-tert-butyldimethylsilyloxy-1,2,6,7,8,8a(R)-hexahydronaphthyl-1(S)]ethyl]-4(R)-tert-butyldimethylsilyloxy-3,4,5,6-tetrahydro-2H-pyran-2-one (2-8)'

To a stirred heterogeneous mixture of alcohol (2-7)' (20.0 g, 34 mmol), anhydrous LiBr (14.7 g, 0.17 mol dried at 125° C. for 16 hours at 0.05 mmHg), 4-dimethylaminopyridine (0.62 g, 5.1 mmol), and dry pyridine (43 mL) at 25° C. was added 2,2-dimethylbutyryl chloride (9.6 mL, 79 mmol). The resulting mixture was then stirred vigorously at 80° C. for 3.0 hours. The cooled reaction mixture was diluted with ether, washed with H₂O and brine, dried (MgSO₄), and concentrated. Flash chromatography (silica, 10% ethyl acetate/hexanes) furnished ester (2-8) as a colorless foam.

TLC Rf=0.60 (20% ethyl acetate/hexanes); ¹H NMR (CDCl₃) δ5.99 (d, J=10 Hz, 1H), 5.78 (dd, J=10 and 6 Hz, 1H), 5.45 (m, 2H), 4.57 (m, 1H), 4.30 (m, 1H), 3.50 (m, 2H), 2.57 (m, 2H), 2.38 (m, 1H), 2.25 (m, 1H), 2.08 (m, 1H), 1.95–1.25 (m), 1.14 (s, 3H), 1.13 (s, 3H), 1.11 (d, J=7H, 3H), 0.90 (s, 18H), 0.89 (d, J=7 Hz, 3H), 0.83 (t=7 Hz, 3H), 0.07 (s, 3H), 0.07 (s, 3H), 0.05 (s, 3H), 0.05 (s, 3H).

Step E: Preparation of 6(R)-[2-[8(R)-(2,2-dimethylbutyryloxy)-2(S)-methyl-6(S)-methyl-7(S)-hydroxymethyl-1,2,6,7,8,8a(R)-hexahydronaphthyl-1(S)]ethyl]-4(R)-hydroxy-3,4,5,6-tetrahydro-2H-pyran-2-one (2-9)'

A mixture of bis-silyl ether (2-8)' (19.6 g, 29 mmol), acetonitrile (400 mL), and 48% HF (20 mL) was stirred vigorously in a plastic container for 3.5 hours at 25° C. The reaction mixture was then carefully poured into a stirring mixture of ether and saturated. NaHCO$_3$. After gas evolution ceased, the organic portion was washed with H$_2$O and brine, dried (MgSO$_4$), and concentrated. Flash chromatography (silica, 70% ethyl acetate/hexanes) gave diol (2-9)' as a colorless foam.

TLC R$_f$=0.24 (80% ethyl acetate/hexanes); $^1$H NMR (CDCl$_3$) δ6.00 (d, J=10 Hz, 1H), 5.81 (dd, J=10 and 6 Hz, 1H), 5.48 (m, 2H), 4.64 (m, 1H), 4.39 (m, 1H), 3.58 (m, 2H), 2.77 (dd, J=18 and 4 Hz, 1H), 2.65 (m, 2H), 2.4 (m, 1H), 2.29 (m, 1H), 2.2–1.3 (m), 1.15 (s, 3H), 1.14 (s, 3H), 1.14 (d, J=7 Hz, 3H), 0.91 (d, J=7 Hz, 3H), 0.85 (t=J=7 Hz, 3H).

EXAMPLE 3

Preparation of 6(R)-[2-[8(R)-(2,2-dimethylbutyryloxy)-2(S)-methyl-6(S)-methyl-7(R)-methyl-1,2,6,7,8,8a(R)-hexahydronaphthyl-1(S)]ethyl]-4(R)-hydroxy-3,4,5,6-tetrahydro-2H-pyran-2-one (3-9)'

Step A: Preparation of N-butyl-7-[1,2,6,7,8,8a(R)-hexahydro-2(S),6(R)-dimethyl-8(S)-(hydroxy)-1(S)-naphthyl]-3(R)-hydroxy-5(R)-hydroxyheptanoic acid amide (3-2)'

A stirred solution of the alcohol (1-2)' from Example 1 Step B (15 g, 45 mmol) and sieve dried butylamine (50 mL) was heated at 80° C. for 1.0 hours. Removal of the heating bath followed by evaporation of the butylamine in vacuo furnished an orange oil. The resulting oil was diluted with ether, washed with 1N HCl (2×) and brine, dried (MgSO$_4$), and concentrated to give butylamide (3-2)' as an orange oil, which was used directly in the next reaction. TLC R$_f$=0.10 (ethyl acetate).

Step B: Preparation of N-butyl-7-[1,2,6,7,8,8a(R)-hexahydro-2(S),6(R)-dimethyl-8(S)-(hydroxy)-1(S)-naphthyl]-3(R)-tert-butyldimethylsilyloxy-5(R)-tert-butyldimethylsilyloxyheptanoic acid amide (3-3)'

To a stirred mixture of triol (3-2)' (21.8 g, 57 mmol), imidazole (17.0 g, 0.25 mol), and DMF (114 mL) at 0° C. was added tert-butyldimethylsilyl chloride (19.0 g, 0.13 mol). After 30 minutes, the cooling bath was removed and the solution allowed to stir overnight. After 20 hours the reaction mixture was diluted with ether, washed with H$_2$O (2×) and brine, dried (MgSO$_4$), and concentrated to give (3-3)' as an orange oil.

TLC R$_f$=0.18 (5% acetone/toluene); $^1$H NMR (CDCl$_3$) δ6.50 (m, 1H), 5.99 (d, J=10 Hz, 1H), 5.82 (dd, J=10 and 6 Hz, 1H), 5.55 (m, 1H), 4.23 (m, 1H), 4.17 (m, 1H), 3.74 (m, 1H), 3.3 (m, 1H), 3.2 (m, 1H), 2.55–1.3 (m), 1.20 (d, J=7 Hz, 3H), 0.92 (m, 24H), 0.09 (s, 3H), 0.07 (s, 3H), 0.06 (s, 6H).

Step C: Preparation of N-butyl-7-[1,2,6,7,8a(R)-pentahydro-2(S),6(R)-dimethyl-8-oxo-1(S)-naphthyl]-3(R)-tert-butyldimethylsilyloxy-5(R)-tert-butyldimethylsilyloxyheptanoic acid amide (3-4)'

To a stirred solution of oxalyl chloride (0.60 mL, 6.9 mmol) in CH$_2$Cl$_2$ (25 mL) at −78° C. was added DMSO (0.65 mL, 9.2 mmol) dropwise. After 5 minutes the alcohol (3-3)' (2.8 g, 4.6 mmol) in CH$_2$Cl$_2$ (20 mL) was added in a stream. After stirring for 30 minutes triethylamine (2.5 mL, 17.9 mmol) was added dropwise followed by removal of the cooling bath. After 20 minutes the reaction mixture was diluted with ethyl acetate, washed with H$_2$O and brine, dried (MgSO$_4$), and concentrated. Flash chromatography (silica, 15% ethyl acetate/hexanes) gave ketone (3-4)' as a colorless oil.

TLC R$_f$=0.25 (5% acetone/toluene); $^1$H NMR (CDCl$_3$) δ6.50 (m, 1H), 5.99 (d, J=10 Hz, 1H), 5.80 (dd, J=10 and 6 Hz, 1H), 5.47 (m, 1H), 4.13 (m, 1H), 3.7 (m, 1H), 3.3 (m, 1H), 3.2 (m, 1H), 2.8 (m, 1H), 2.45–1.3 (m), 1.14 (d, J=7 Hz, 3H), 0.90 (m, 24H), 0.09 (s, 3H), 0.07 (s, 3H), 0.06 (s, 6H).

Step D: Preparation of N-butyl-N-methyl-7-[1,2,6,7,8a(R)-pentahydro-2(S),6(R),7(R)-trimethyl-8-oxo-1(S)-naphthyl]-3(R)-tertbutyldimethylsilyloxy-5(R)-tert-butyldimethylsilyloxyheptanoic acid amide (3-5)'

To a stirred mixture of ketone (3-4)' (0.27 g, 0.44 mmol) and dry THF (2.2 mL) at −78° C. was added lithium bis(trimethylsilyl)amide (0.92 mL, 0.92 mmol, 1M in THF) dropwise. After 10 minutes methyl iodide (30 μL, 0.48 mmol) was added and the reaction was warmed to −25° C. Additional methyl iodide (60 μL, 0.96 mmol) was added and the reaction quenched with ether and H$_2$O after 5 minutes. The organic portion was washed with H$_2$O (2×) and brine, dried (MgSO$_4$), and concentrated. Flash chromatography (silica, 12% ethyl acetate/hexanes) gave (3-5)' as a colorless oil.

TLC R$_f$=0.4 (20% ethyl acetate/hexanes); $^1$H NMR (CDCl$_3$) δ5.99 (d, J=10 Hz, 1H), 5.75 (dd, J=10 and 6 Hz, 1H), 5.41 (bs, 1H), 4.28 (m, 1H), 3.72 (m, 1H), 3.44 (m, 1H), 3.2 (m, 1H), 3.0 (s, 1.5H), 2.9 (s, 1.5H), 2.71 (bd, J=11 Hz, 1H), 2.45–2.1 (m, 5H), 1.92 (m, 1H), 1.75–1.25 (m), 1.17 (d, J=7 Hz, 3H), 1.13 (d, J=7 Hz, 3H), 0.90 (m, 24H), 0.07 (s, 3H), 0.05 (s, 3H), 0.03 (s, 6H).

Step E: Preparation of N-butyl-N-methyl-7-[1,2,6,7,8,8a(R)-hexahydro-2(S),6(S),7(S)-trimethyl-8(S)-hydroxy-1(S)-naphthyl]-3(R)-tert-butyldimethylsilyloxy-5(R)-tertbutyldimethylsilyloxyheptanoic acid amide (3-6)'

To a stirred solution of ketone (3-5)' (0.67 g, 1.1 mmol), THF (10 mL), and H$_2$O (1.0 mL) at 0° C. was added NaBH$_4$ (40 mg, 1.1 mmol). After 1.0 hour the reaction mixture was diluted with ether, washed with H$_2$O (2×) and brine, dried (MgSO$_4$), and concentrated. Flash chromatography (12% ethyl acetate/hexanes) gave alcohol (3-6)' as an oil. TLC R$_f$=0.31 (20% ethyl acetate/hexanes); $^1$H NMR (CDCl$_3$) δ5.95 (d, J=10 Hz, 1H), 5.77 (dd, J=10 and 6 Hz, 1H), 5.44 (bs, 1H), 4.28 (m, 1H), 3.86 (m, 1H), 3.8 (m, 1H), 3.39 (m, 1H), 3.19 (m, 1H), 2.97 (s, 1H), 2.87 (s, 1H), 2.42 (m, 3H), 2.13 (bd, J=11 Hz, 1H), 2.0–1.2 (m), 1.17 (d, J=7 Hz, 3H), 0.9 (m, 27H), 0.07 (s, 3H), 0.05 (s, 3H), 0.04 (s, 6H).

Step F: Preparation of N-butyl-N-methyl-7-[1,2,6,7,8,8a(R)-hexahydro-2(S),6(S),7(R)-trimethyl-8(S)-(2,2-dimethylbutyryloxy)-1(S)-naphthyl]-3(R)-tert-butyldimethylsilyloxy-5(R)-tert-butyldimethylsilyloxyheptanoic acid amide (3-7)'

To a stirred heterogeneous mixture of alcohol (3-6)' (0.40 g, 0.64 mmol), anhydrous LiBr (0.3 g, 3.5 mmol), 4-dimethylaminopyridine (12 mg, 0.1 mmol), and dry pyridine (800 µL) was added 2,2-dimethylbutyryl chloride (0.22 mL, 1.8 mmol). The resulting mixture was stirred vigorously at 50° C. for 2.0 hours. The cooled reaction mixture was diluted with ether, washed with H$_2$O and brine, dried (MgSO$_4$), and concentrated. Flash chromatography (silica, 15% ethyl acetate/hexanes) furnished ester (3-7)' as a colorless foam.

TLC R$_f$=0.63 (20% ethyl acetate/hexanes); $^1$H NMR (CDCl$_3$) δ6.03 (d, J=10 Hz, 1H), 5.8 (dd, J=10 and 6 Hz, 1H), 5.1 (bs, 1H), 4.39 (m, 1H), 3.63 (m, 1H), 3.56 (m, 1H), 3.2 (m, 1H), 3.09 (s, 1H), 2.96 (s, 1H), 2.6 (m, 1H), 2.47 (m, 1H), 2.4 (dd, J=14 and 4 Hz, 1H), 2.31 (bd, J=11 Hz, 1H), 2.05 (m, 2H), 1.8–1.2 (m), 1.17 (s, 6H), 1.14 (d, J=7 Hz, 3H), 1.04 (d, J=7 Hz, 3H), 0.90 (m, 24H).

Step G: Preparation of N-butyl-N-methyl-7-[1,2,6,7,8,8a(R)-hexahydro-2(S),6(S),7(R)-trimethyl-8(S)-(2,2-dimethylbutyryloxy)-1(S)-naphthyl]-3(R)-hydroxy-5(R)-hydroxyheptanoic acid amide (3-8)'

A mixture of bis-silyl ether (3-7)' (270 mg, 0.37 mmol), acetonitrile (1.8 mL), and 48% HF (100 µL) at 25° C. was stirred vigorously in a plastic container. The reaction mixture was then carefully poured into a stirred mixture of ether and sat. NaHCO$_3$. After gas evolution ceased, the organic portion was washed with H$_2$O and brine, dried (MgSO$_4$), and concentrated. Flash chromatography (silica, 80% ethyl acetate/hexanes) gave diol (3-8)' as an oil.

TLC R$_f$=0.22 (80% ethyl acetate/hexanes); $^1$H NMR (CDCl$_3$) δ5.99 (d, J=10 Hz, 1H), 5.8 (dd, J=10 and 6 Hz, 1H), 5.46 (bs, 1H), 5.1 (bs, 1H), 4.28 (m, 1H), 3.81 (m, 1H), 3.38 (m, 1H), 3.25 (m, 1H), 2.97 (s, 15H), 2.94 (s, 1.5H), 2.42 (m, 2H), 2.19 (bd, J=11 Hz, 1H), 2.0 (m, 2H), 1.75–1.1 (m), 1.0–0.8 (m).

Step H: Preparation of 6(R)-[2-[8(R)-(2,2-dimethylbutyryloxy)-2(S)-methyl-6(S)-methyl-7(R)-methyl-1,2,6,7,8,8a(R)-hexahydronaphthyl-1(S)]ethyl]-4(R)-hydroxy-3,4,5,6-tetrahydro-2H-pyran-2-one (3-9)'

A mixture of amide (3-8)' (0.14 g, 0.28 mmol), 2N NaOH (0.21 mL), and ethanol (2.1 mL) was refluxed for 2.0 hours. The cooled reaction mixture was acidified with 1N HCl and then extracted with ethyl acetate. The organic portion was washed with 1N HCl, H$_2$O, and brine, dried (MgSO$_4$), and concentrated. The oil was dissolved in acetonitrile (2.0 mL) and treated with 1-(3-dimethylaminopropyl)-3-ethyl-carbodiimide hydrochloride (107 mg, 0.56 mmol). After 1.0 hour the mixture was diluted with ether, washed with H$_2$O and brine, dried (MgSO$_4$), and concentrated. Flash chromatography (silica, 70% ethyl acetate/hexanes) gave lactone (3-9)' as a colorless foam. This was rechromatographed (silica, 15% acetone/hexane) to furnish pure (3-9)'.

TLC R$_f$=0.46 (80% ethyl acetate/hexanes); $^1$H NMR (CDCl$_3$) δ5.99 (d, J=10 Hz, 1H), 5.81 (dd, J=10 and 6 Hz, 1H), 5.47 (m, 1H), 5.10 (m, 1H), 4.62 (m, 1H), 4.39 (m, 1H), 2.75 (dd, J=18 and 5 Hz, 1H), 2.62 (m, 1H), 2.38 (m, 1H), 2.29 (m, 1H), 2.1–1.2 (m), 1.13 (s, 3H), 1.12 (s, 3H), 1.11 (d, J=7 Hz, 3H), 1.0 (d, J=7 Hz, 3H), 0.91 (d, J=7 Hz, 3H), 0.83 (t, J=7 Hz, 3H).

EXAMPLE 4

Preparation of 6R-[2-[8(R)-(2,2-dimethylbutyryloxy)-2(S)-methyl-6(S)-methyl-7(S)-(1(S)-hydroxyethyl)-1,2,6,7,8,8a(R)-hexahydronaphthyl-1(S)]ethyl]-4(R)-hydroxy-3,4,5,6-tetrahydro-2H-pyran-2-one(4-9)' and 6R-[2-[8(R)-(2,2-dimethylbutyryloxy)-2(S)-methyl-6(S)-methyl-7(S)-(1(R)-hydroxyethyl)-1,2,6,7,8,8a(R)-hexahydronaphthyl-1(S)]ethyl]-4(R)-hydroxy-3,4,5,6-tetrahydro-2H-pyran-2-one(4-9a)'

Step A: Preparation of 6(R)-[2-[8-trimethylsilyloxy-2(S)-methyl-6(S)-methyl-1,2,6,8a(R)-tetrahydronaphthyl-1(S)]ethyl]-4(R)-tert-butyldimethylsilyloxy-3,4,5,6-tetrahydro-2H-pyran-2-one-(1-4)'

To a stirred solution of ketone (1-3)' (24 g, 59 mmol), triethylamine (41.1 mL, 0.29 mol), and CH$_2$Cl$_2$ (300 mL) at 0° C. was added trimethylsilyltriflate (22.9 mL, 0.12 mol) portionwise over a 5 minute period. After 30 minutes the cooling bath was removed and H$_2$O (50 mL) was added to the reaction mixture. After stirring for 5 minutes the reaction mixture was diluted with ether, washed with H$_2$O and brine, dried (MgSO$_4$), and concentrated. Flash chromatography (silica, 12% ethyl acetate/hexanes) gave (1-4)' as a colorless oil.

TLC Rf=0.46 (20% ethyl acetate/hexanes); $^1$H NMR (CDCl$_3$) 5.99(d,J=10 Hz,1H), 5.61(dd,J=10 and 5 Hz,1H), 5.32(m,1H), 4.84(dd,J=4 and 1 Hz,1H), 4.62(m,1H), 4.27(m,1H), 2.9(m,1H), 2.63–2.52(m,3H), 2.3(m,1H), 1.95–1.45(m), 1.01(d,J=7 Hz,3H), 0.91(d,J=7 Hz,3H), 0.85(S,9H), 0.16(S,9H), 0.04(S,3H), 0.03(S,3H).

Step B: Preparation of 6R-[2-[8-oxo-2(S)-methyl-6(S)-methyl-7(S)-(1(S)-hydroxyethyl)-1,2,6,7,8,8a(R)-hexahydronaphthyl-1(S)]ethyl]-4(R)-tert-butyldimethylsilyloxy-3,4,5,6-tetrahydro-2H-pyran-2-one(4-5)' and 6R-[2-[8-oxo-2(S)-methyl-6(S)-methyl-7(S)-(1(R)-hydroxyethyl)-1,2,6,7,8,8a(R)-hexahydronaphthyl-1(S)]ethyl]-4(R)-tert-butyldimethylsilyloxy-3,4,5,6-tetrahydro-2H-pyran-2-one(4-5a)'

1.90 g TiCl$_4$ (0.01 moles) was added to CH$_2$Cl$_2$ (150 ml) at −74° C. under nitrogen. Acetaldehyde was added to the CH$_2$Cl$_2$ solution dropwise while maintaining the temperature below −70° C. The mixture was stirred for a few minutes and then the silyl enol ether (1-4)' (5.05 g, 0.01 mole) was added dropwise while maintaining the temperature below −68° C. The mixture was stirred for about 1 hour and the temperature allowed to rise to −50° C. The reaction mixture was quenched with 20 ml of H$_2$O at −50° C. and then diluted with 1200 ml of ether. The organic layer was separated and washed with H$_2$O (4×250 ml) and saturated NaCl (250 ml) and dried (anhydrous Na$_2$SO$_4$). The mixture was filtered and the solvent evaporated to yield a viscous residue. The residue was chromatographed on a still column (90 mm, 7½" bed of silica gel) and eluted with ethyl acetate/hexanes (30:70). Compound (4-5)' eluted first from the column (R$_f$=0.5) and after solvent removal crystallized on standing m.p.

75.5°–79° C. Compound (4-5a)' eluted later from the column (R$_f$=0.3) and after solvent removal was obtained as an amorphous solid.

Step C: Preparation of
6(R)-[2-[8(R)-hydroxy-2(S)-methyl-6(S)-methyl-7(S)-(1(S)-hydroxyethyl)-1,2,6,7,-8,8a(R)-hexahydronaphthyl-1(S)]-ethyl]-4(R)-tertbutyldimethylsilyloxy-3,4,5,6-tetrahydro-2H-pyran-2-one. (4-6)'

To a solution of ketone (4-5)' in H$_2$O/THF (110 ml, 1:10) was added PdCl$_2$ (1.95 g, 0.011 mole) and the mixture cooled to −30° C. NaBH$_4$ (2.90 g, 0.055 mole) was added in one portion and the temperature allowed to rise to 0° C. over 1 hour. The reaction mixture was diluted with 600 ml of ether and 250 ml of water, the layers separated and the aqueous layer extracted with 200 ml ether. The combined organic portions were washed with H$_2$O (3×200 ml) followed by saturated NaCl (200 ml) and dried (anhydrous Na$_2$SO$_4$). The mixture was filtered and the solvent evaporated to obtain a viscous residue which was dissolved in 20 ml ethyl acetate/hexanes (1:1). The mixture was gradually diluted with 200 ml of hexanes and the precipated white solid collected. m.p. 124°–126.5° C.

Step D: Preparation of
6R-[2-[8(R)-hydroxy-2(S)-methyl-6(S)-methyl-7(S)-(1(S)-tert-butyldimethylsilyloxyethyl)-1,2,6,7,8,8a(R)-hexahydronaphthyl-1(S)]-ethyl]-4(R)-tertbutyldimethylsiloxy-3,4,5,6-tetrahydro-2H-pyran-2-one. (4-7)'

The diol (4-6)' (21.5 g, 0.045 mol) from Step C was dissolved in CH$_2$Cl$_2$ (300 ml) and cooled to −10° C. and 2,6-lutidine (11.0 g, 0.1 mol) added followed by the dropwise addition of TBDMSOTf (12.4 g, 0.047 mol). The mixture was stirred at −10° C. for 35 minutes; the solution was quenched by the addition of ~100 ml of H$_2$O and diluted with 500 ml CH$_2$Cl$_2$. The CH$_2$Cl$_2$ layer was separated and washed with 2×200 ml portions H$_2$O followed by 4×200 ml portions of 1N HCl and finally with 200 ml saturated NaCl. The CH$_2$Cl$_2$ layer was dried (anhydrous Na$_2$SO$_4$) and filtered and the solvent removed in vacuo to yield a viscous residue. The residue was chromatographed through a Still column (120 mm, 8½" bed silica gel) eluting with 20% EtOAc/hexanes. The product containing fractions were combined and the solvent removed in vacuo to obtain (4-7)' as a colorless oil. R$_f$=0.25, in 20% EtOAc/hexanes.

Step E: Preparation of
6R-[2-[8(R)-(2,2-dimethylbutyryloxy)-2(S)-methyl-6(S)-methyl-7(S)-(1(S)-tert-butyldimethylsilyloxyethyl)-1,2,6,7,8,8a(R)-hexahydronaphthyl-1(S)]-ethyl]-4(R)-tertbutyldimethylsilyoxy-3,4,5,6-tetrahydro-2H-pyran-2-one. (4-8)'

To a stirred mixture of (4-7)' (0.94 g, 1.6 mmol), anhydrous LiBr (0.72 g, 8.3 mmol dried at 125° C. for 16 hours at 0.05 mm Hg), 4-dimethylaminopyridine (30 mg, 0.2 mmol), and pyridine (2.0 ml) at 25° C. was added 2,2-dimethylbutyryl chloride (0.57 ml, 4.1 mmol) followed by heating at 80° C. for 3.0 hours. The cooled reaction mixture was diluted with ether, washed with H$_2$O and brine, dried (MgSO$_4$), and concentrated. Flash chromatography (silica, 10% ethyl acetate/hexanes) gave (4-8)' as an oil. R$_f$=0.68, in 20% EtOAc/hexanes.

Step F: Preparation of
6R1[2-[8(R)-(2,2-dimethylbutyryloxy)-2(S)-methyl-6(S)-methyl-7(S)-(1(S)-hydroxyethyl)-1,2,6,7,8,8a(R)-hexahydronaphthyl-1(S)ethyl]-4(R)-hydroxy-3,4,5,6-tetrahydro-2H-pyran-2-one. (4-9)'

To a vigorously stirred solution of (4-8)' from Step E (4.7 g, 7.1 mmol) and acetonitrile (70 ml) in a plastic container at 25° C. was added 48% HF (30 ml, 70 mmol). After 30 minutes additional 48% HF (5.0 ml) was added. After 30 minutes the reaction mixture was carefully poured into a vigorously stirred mixture of saturated NaHCO$_3$ and ether. After gas evolution subsided the organic portion was washed with H$_2$O (2×) and brine, dried (MgSO$_4$), and concentrated. Flash chromatography (silica, 70% ethyl acetate/hexanes) gave (4-9)' as a foam. The product was crystallized from EtOAc/hexanes to give a colorless powder.

$^1$H NMR (CDCl$_3$, 300 MHz) δ0.82 (t,3H), 0.88 (d,3H), 1.10 (m, 9H), 1.3 (d,3H), 1.3–2.15 (m, 13H), 2.3–2.45 (m,2H), 2.45–2.81 (m,3H), 3.48–3.63(m,1H), 4.3–4.41 (m, 1H), 4.55–4.69 (m,1H), 5.42 (m,1H), 5.42 (m,1H), 5.71 (m,1H) 5.8 (dd), 5.98 (d,1H).

Step G: Preparation of
6R-[2-[8(R)-(2,2-dimethylbutyryloxy)-2(S)-methyl-6(S)-methyl-7(S)-(1(R)-hydroxyethyl)-1,2,6,7,8,8a(R)-hexahydronaphthyl-1(S)ethyl]-4(R)-hydroxy-3,4,5,6-tetrahydro-2H-pyran-2-one. (4-9a)'

This compound was prepared from compound (4-5a)' employing Steps 4C-4F in an analogous manner as for the transformation of compound (4-5)' to compound (4-9)'.

$^1$H NMR (CDCl$_3$, 300 MHz) 0.82 (t,3H), 0.88 (t,3H), 1.12 (m,9H), 1.32 (d,3H), 1.3–2.05 (m, 13H), 2.22–2.45 (m,2H), 2.45–2.82 (m,3H), 3.72 (m,1H), 4.38 (m, 1H), 4.61 (m,1H), 5.3 (m,1H), 5.50 (m,1H), 5.79 (m,1H) 6.01 (mp1H).

EXAMPLE 5

Preparation of
6(R)-[2-[8(R)-(2,2-dimethylbutyryloxy)-2(S)-methyl-6(S)-methyl-7(S)-(1(S)-hydroxybenzyl)-1,2,6,7,8,8a(R)-hexahydronaphthyl-1(S)ethyl]-4(R)-hydroxy-3,4,5,6-tetrahydro-2H-pyran-2-one. (4-9)"

Step A: Preparation of
6(R)-[2-[8-trimethylsilyloxy-2(S)-methyl-6(S)-methyl-1,2,6,8a(R)-tetrahydronaphthyl-1(S)]ethyl]-4(R)-tert-butyldimethylsilyloxy-3,4,5,6-tetrahydro-2H-pyran-2-one(1-4)'

To a stirred solution of ketone (1-3)' (24 g, 59 mmol), triethylamine (41.1 mL, 0.29 mol), and CH$_2$Cl$_2$ (300 mL) at 0° C. was added trimethylsilyltriflate (22.9 mL, 0.12 mol) potionwise over a 5 minute period. After 30 minutes the cooling bath was removed and H$_2$O (50 mL) was added to the reaction mixture. After stirring for 5 minutes the reaction mixture was diluted with ether, washed with H$_2$O and brine, dried (MgSO$_4$), and concentrated. Flash chromatography (silica, 12% ethyl acetate/hexanes) gave (1-4)' as a colorless oil.

TLC R$_f$=0.46 (20% ethyl acetate/hexanes); $^1$HNMR (CDCl$_3$) 5.99(d,J=10 Hz,1H), 5.61(dd,J=10 and 5 Hz,1H), 5.32(m,1H), 4.84(dd,J=4 and 1 Hz,1H), 4.62(m,1H), 4.27(m,1H), 2.90(m,1H), 2.63–2.52(m,3H), 2.3(m,1H), 1.95–1.45(m), 1.01(d,J=7 Hz,3H), 0.91(d,J=7 Hz,3H), 0.85(S,9H), 0.16(S,9H), 0.04(S,3H), 0.03(S,3H).

Step B: Preparation of 6(R)-[2-[8-oxo-2(S)-methyl-6(S)-methyl-7(S)-(1(S)-hydroxybenzyl)-1,2,6,7,8,8a(R)-hexahydronaphthyl-1(S)]ethyl]-4(R)-tertbutyldimethylsilyloxy-3,4,5,6-tetrahydro-2H-pyran-2-one. (4-5)″

5.69 g $TiCl_4$ (0.03 mmol) was added $CH_2Cl_2$ (300 ml) at −74° C. under nitrogen. Benzaldehyde was added to the $CH_2Cl_2$ solution dropwise while maintaining the temperature below −70° C. The mixture was stirred for a few minutes and then the silyl enol ether (1-4)′ (15.15 g, 0.03 mole) in $CH_2Cl_2$ (25 ml) was added dropwise while maintaining the temperature below −70° C. The mixture was stirred for ~2 hours and then allowed to warm to −30° C. over 45 minutes. The mixture was quenched with 50 ml of $H_2O$ and the mixture diluted with 700 ml $CH_2Cl_2$ and 150 ml of 2 $H_2O$. The organic phase was separated, washed with water (3×150 ml) saturated NaCl (150 ml), and dried ($Na_2SO_4$). The mixture was filtered and the solvent removed in vacuo to give a viscous residue. The residue was chromatographed through a still column (90 mm width, 8″ bed of silica gel) while eluting with 25% EtOAc/hexanes, hexane:acetone. The product fractions were combined and the solvent removed in vacuo to obtain (4-5)″ as a solid residue. The solid was washed with 75 ml of hexane and dried. m.p. 170°–174° C.

Step C: Preparation of 6(R)-[2-[8(R)-hydroxy-2(S)-methyl-6(S)-methyl-7(S)-(1(S)-hydroxybenzyl)-1,2,6,7,8,8a(R)-hexahydronaphthyl-1(S)]ethyl]-4(R)-tertbutyldimethylsilyloxy-3,4,5,6-tetrahydro-2H-pyran-2-one. (4-6)″

To a solution of the ketone (4-5)″ (4.5 g, 0.00835 mole) in $THF/H_2O$ (10:1, 100 ml) was added $PdCl_2$ (1.60 g, 0.009 mole) and the mixture cooled to −35° C. $NaBH_4$ (3.42 g, 0.09 mole) was added in one portion and the temperature allowed to rise to −25° C. and then after 1½ hours to 0° C. The reaction mixture was diluted with 400 ml of ether and 150 ml of $H_2O$; 1N HCl was added until gas evolution subsided and the layers were separated. The aqueous layer was extracted with 150 ml of ether and the ether extracts combined and washed with water (4×100 ml), saturated NaCl (100 ml) and dried ($Na_2SO_4$). The mixture was filtered to obtain a viscous residue which was chromatographed through a Still column (60 mm width, 7½″ bed silica gel) while eluting with hexane/EtOAc (70:30). The product fractions were combined and evaporated to yield a (4-6)″ as a white solid residue. $R_f$=0.42 in 50% EtOAc/hexanes.

Step D: Preparation of 6R-[2-[8(R)-hydroxy-2(S)-methyl-6(S)-methyl-7(S)-(1(S)-tert-butyldimethylsilyloxybenzyl)-1,2,6,7,8,8a(R)-hexahydronaphthyl-1(S)]ethyl]-4(R)-tertbutyldimethylsilyoxy-3,4,5,6-tetrahydro-2H-pyran-2-one. (4-7)″

The diol (4-6)″ (21.5 g, 0.045 mol) was dissolved in $CH_2Cl_2$ (300 ml) and cooled to −10° C. and 2,6-lutidine (11.0 g, 0.10 mol) added followed by dropwise addition of TBDMSOTf (12.4 g, 0.047 mol). The mixture was stirred at −10° C. for 35 minutes; the solution was quenched by the addition of ~100 ml of $H_2O$ and diluted with 500 ml $CH_2Cl_2$. The $CH_2Cl_2$ layer was separated and washed with 2×200 ml portions $H_2O$ followed by 4×200 ml portions of 1N HCl and finally with 200 ml saturated NaCl. The $CH_2Cl_2$ layer was dried (anhydrous $Na_2SO_4$) and filtered and the solvent removed in vacuo to yield a viscous residue. The residue was chromatographed through a still column (120 mm, 8½″ bed silica gel) eluting with 20% EtOAc/hexanes. The product containing fractions were combined and the solvent removed in vacuo to obtain (4-7)″ as a colorless residue. $R_f$=0.54, in 30% EtOAc/hexanes.

Step E: Preparation of 6R-[2-[8(R)-(2,2-dimethylbutyryloxy)-2(S)-methyl-6(S)-methyl-7(S)-(1(S)-tert-butyldimethylsilyloxybenzyl)-1,-2,6,7,8,8a(R)-hexahydronaphthyl-1(S)]-ethyl]-4(R)-tertbutylmethylsilyoxy-3,4,5,6-tetrahydro-2H-pyran-2-one. (4-8)″

To a stirred mixture of (4-7)″ (0.94 g, 1.6 mmol), anhydrous LiBr (0.72 g, 8.3 mmol dried at 125° C. for 16 hours at 0.05 mm Hg), 4-dimethylaminopyridine (30 mg, 0.2 mmol), and pyridine (2.0 ml) at 25° C. was added 2,2-dimethylbutyryl chloride (0.57 ml, 4.1 mmol) followed by heating at 80° C. for 3.0 hours. The cooled reaction mixture was diluted with ether, washed with $H_2O$ and brine, dried ($MgSO_4$), and concentrated. Flash chromatography (silica, 10% ethyl acetate/hexanes) gave (4-8)″ as an oil. $R_f$=0.45, in 20% EtOAc/hexanes.

Step F: Preparation of 6R-[2-[8(R)-(2,2-dimethylbutyryloxy)-2(S)-methyl-6(S)-methyl-7(S)-(1(S)-hydroxybenzyl)-1,2,6,7,8,8a(R)-hexahydronaphthyl-1(S)]-ethyl]-4(R)-hydroxy-3,4,5,6-tetrahydro-2H-pyran-2-one. (4-9)″

To a vigorously stirred solution of (4-8)″ (4.7 g, 7.1 mmol) and acetonitrile (70 ml) in a plastic container at 25° C. was added 48% HF (30 ml, 70 mmol). After 30 minutes additional 48% HF (5.0 ml) was added. After 30 minutes the reaction mixture was carefully poured into a vigorously stirred mixture of saturated $NaHCO_3$ and ether. After gas evolution subsided the organic portion was washed with $H_2O$ (2X) and brine, dried ($MgSO_4$), and concentrated. Flash chromatography (silica, 70% ethyl acetate/hexanes) gave (4-9)″ product as a foam. The product was crystallized from ethyl acetate/hexanes to give (4-9)″ a colorless powder.

$^1$H NMR ($CDCl_3$, 300 MHz) δ0.8–0.92(m,6H), 0.95 (d,3H), 1.12 (s,6H), 1.2–2.55 (m, 15H), 2.55–2.8 (m,2H), 2.58–2.7(m,1H), 4.3–4.42 (m,2H), 5.39 (m, 1H), 5.83,(dd,1H), 5.89 (m,1H), 6.01 (d,1H), 7.25–7.46 (m,5H).

The following compounds can be prepared following schemes 1–4 and examples 1–5. Compounds 6–10 which are dialkylated at the 7-position can be prepared by a second alkylation of compound (3-5) in scheme 3. Compounds 21–25 are prepared by employing a dihaloalkane in the sequence (3-4) to (3-5) of scheme 3.

EXAMPLES 6–25

|     | $R_4$           | $R_2$       | $R_3$  |
| --- | --------------- | ----------- | ------ |
| 6.  | β-$CH_3$        | —$CH_3$     | —$CH_3$ |
| 7.  | H               | —$CH_3$     | —$CH_3$ |
| 8.  | β-OH            | —$CH_3$     | —$CH_3$ |
| 9.  | α-$CH_2OH$      | —$CH_3$     | —$CH_3$ |
| 10. | β-$CH_2OH$      | —$CH_3$     | —$CH_3$ |
| 11. | β-$CH_3$        | —$CH_2OH$   | —H     |
| 12. | H               | —$CH_2OH$   | —H     |
| 13. | β-OH            | —$CH_2OH$   | —H     |
| 14. | α-$CH_2OH$      | —$CH_2OH$   | —H     |
| 15. | β-$CH_2OH$      | —$CH_2OH$   | —H     |
| 16. | β-$CH_3$        | —$CO_2CH_2$ | —H     |
| 17. | H               | —$CO_2CH_3$ | —H     |
| 18. | β-OH            | —$CO_2CH_3$ | —H     |
| 19. | α-$CH_2OH$      | —$CO_2CH_3$ | —H     |
| 20. | β-$CH_2OH$      | —$CO_2CH_3$ | —H     |

-continued

|     | R₄        | R₂ | R₃         |
|-----|-----------|----|------------|
| 21. | β-CH₃     |    | —(CH₂)₅—   |
| 22. | H         |    | —(CH₂)₅—   |
| 23. | β-OH      |    | —(CH₂)₅—   |
| 24. | α-CH₂OH   |    | —(CH₂)₅—   |
| 25. | β-CH₂OH   |    | —(CH₂)₅—   |

EXAMPLE 26

Preparation of Ammonium Salts of Compounds II

The lactone (1.0 mmol) from Example 1 Step I is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO₄). The MgSO₄ is removed by filtration and the filtrate saturated with ammonia (gas) to give the ammonium salt.

EXAMPLE 27

Preparation of Alkali and Alkaline Earth Salts of Compounds II

To a solution of 44 mg of lactone from Example 1 Step I in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 28

Preparation of Ethylenediamine Salts of Compounds II

To solution of 0.5 g of the ammonium salt from Example 26 in 10 ml of methanol is added 0.04 ml of ethylenediamine. The methanol is stripped off under vacuum to obtain the desired ethylenediamine salt.

EXAMPLE 29

Preparation of Tris(hydroxymethyl)aminomethane Salts of Compounds II

To a solution of 202 mg of the ammonium salt from Example 26 in 5 ml of methanol is added a solution of 50 mg of tris(hydroxymethyl)aminomethane is 5 ml of methanol. The solvent is removed in vacuo to afford the desired tris(hydroxymethyl)aminomethane salt.

EXAMPLE 30

Preparation of L-Lysine Salts of Compounds II

A solution of 0.001 mole of L-lysine and 0.0011 mole of the ammonium salt from Example 26 in 15 ml of 85% ethanol is concentrated to dryness in vacuo to give the desired L-lysine salt.

Similarly prepared are the L-arginine, L-ornithine, and N-methyglucamine salts.

EXAMPLE 31

Preparation of Tetramethylammonium Salts of Compounds II

A mixture of 68 mg of ammonium salt from Example 26 in 2 ml of methylene chloride and 0.08 ml of 24% tetramethylammonium hydroxide in methanol is diluted with ether to yield the desired tetramethylammonium salt.

EXAMPLE 32

Preparation of Methyl Esters of Compounds II

To a solution of 400 mg of lactone from Example 1 Step I in 100 ml of absolute methanol is added 10 ml 0.1 M sodium methoxide in absolute methanol. This solution is allowed to stand at room temperature for one hour, then is diluted with water and extracted twice with ethyl acetate. The organic phase is separated, dried (Na₂SO₄), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenethanolm 2-acetamidoethanol and the like, and employing the corresponding alcohol, phenethanol, 2-acetamidoethanol and the like, and employing the corresponding alcohol as solvent, the corresponding esters are obtained.

EXAMPLE 33

Preparation of Free Dihydroxy Acids

The sodium salt of the compound II from Example 27 is dissolved in 2 ml of ethanol-water (1:1; v:v) and added to 10 ml of 1N hydrochloric acid from which the dihydroxy acid is extracted with ethyl acetate. The organic extract is washed once with water, dried (Na₂SO₄), and evaporated in vacuo with a bath temperature not exceeding 30° C. The dihydroxy acid derivative derived slowly reverts to the corresponding parent lactone on standing at room temperature. The dihydroxy acid form can be maintained by increasing the pH above 7.0.

EXAMPLE 34

As a specific embodiment of a composition of this invention, 20 mg of lactone from Example 1 Step I is formulated with sufficient finely divided lactose to provide a total amount of 580 to 590 mg to fill a size 0, hard-gelatin capsule.

What is claimed is:

1. A compound represented by the structural formula (I):

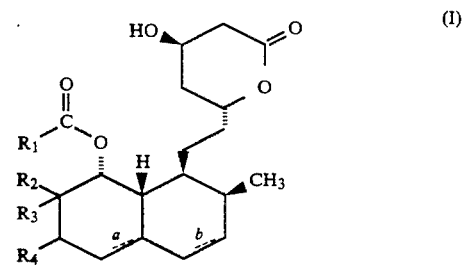

wherein:

$R_1$ is:
  (1) $C_{1-10}$ alkyl;
  (2) substituted $C_{1-10}$ alkyl in which one or more substituent(s) is selected from:
    (a) halogen,
    (b) hydroxy,
    (c) $C_{1-10}$ alkoxy,
    (d) $C_{1-15}$ alkoxycarbonyl,
    (e) $C_{1-5}$ acyloxy,
    (f) $C_{3-8}$ cycloalkyl,
    (g) phenyl, (h) substituted phenyl in which the substituents are X and Y,
(i) $C_{1-10}$ alkylS(O)$_n$,
(j) $C_{3-8}$ cycloalkylS(O)$_n$,
(k) phenylS(O)$_n$,
(l) substituted phenylS(O)$_n$ in which the substituents are X and Y, and
(m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
   (a) $C_{1-10}$ alkyl
   (b) substituted $C_{1-10}$ alkyl in which the substituent is
      (i) halogen,
      (ii) hydroxy,
      (iii) $C_{1-10}$ alkoxy,
      (iv) $C_{1-5}$ alkoxycarbonyl,
      (v) $C_{1-5}$ acyloxy,
      (vi) phenyl,
      (vii) substituted phenyl in which the substituents are X and Y
      (viii) $C_{1-10}$ alkylS(O)$_n$,
      (ix) $C_{3-8}$ cycloalkylS(O)$_n$,
      (x) phenylS(O)$_n$,
      (xi) substituted phenylS(O)$_n$ in which the substituents are X and Y, and
      (xii) oxo,
   (c) $C_{1-10}$ alkylS(O)$_n$,
   (d) $C_{3-8}$ cycloalkylS(O)$_n$,
   (e) phenylS(O)$_n$,
   (f) substituted phenylS(O)$_n$ in which the substituents are X and Y,
   (g) halogen,
   (h) hydroxy,
   (i) $C_{1-10}$ alkoxy,
   (j) $C_{1-5}$ alkoxycarbonyl,
   (k) $C_{1-5}$ acyloxy,
   (l) phenyl, and
   (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from the group consisting of:
   (a) piperidinyl,
   (b) pyrrolidinyl,
   (c) piperazinyl,
   (d) morpholinyl, and
   (e) thiomorpholinyl; and
(17) $R_9$S in which $R_9$ is selected from
   (a) $C_{1-10}$ alkyl,
   (b) phenyl, and
   (c) substituted phenyl in which the substituents are X and Y;

$R_2$ and $R_3$ are each independently selected from the group consisting of:

(1) H;
(2) $R_6$;
$R_6$ is selected from
(1) substituted $C_{1-10}$ alkyl in which one or two substituents are selected from
   (a) amino;
   (b) phenylacyloxy,
   (c) phenoxycarbonyl,
   (d) phenyl$C_{1-5}$alkylacyloxy,
   (e) phenyl$C_{1-5}$alkoxy,
   (f) $C_{1-5}$alkylamino,
   (g) di($C_{1-5}$alkyl)amino,
   (h) phenylamino,
   (i) substituted phenylamino in which the substituents are X and Y,
   (j) phenyl $C_{1-5}$alkylamino,
   (k) substituted phenyl $C_{1-5}$ alkylamino in which the substituents are X and Y,
   (l) substituted phenyl in which the substituents are X and Y,
   (m) phenylS(O)$_n$,
   (n) substituted phenylS(O)$_n$ in which the substituents are X and Y,
   (o) phenyl $C_{1-5}$ alkyl S(O)$_n$,
   (p) $C_{1-5}$ alkylS(O)$_n$,
   (q) phenylaminoacyloxy,
   (r) $C_{1-5}$alkylaminoacyloxy,
   (s) $C_{1-5}$alkylacylamino,
   (t) di(phenyl$C_{1-5}$alkyl)phosphonyl,
   (u) di($C_{1-5}$alkyl)phosphinyl,
   (v) $C_{1-5}$alkyl-carbonyl,
   (w) carboxy-; or
(2) 1(S)-hydroxyethyl;
(3) 1(S)-hydroxybenzyl;
provided that both of $R_2$ and $R_3$ are not H;
$R_4$ is
(1) hydrogen;
(2) hydroxy;
(3) $C_{1-10}$ alkyl; and
(4) substituted $C_{1-10}$ alkyl in which one or more substituents is selected from
   (a) halogen,
   (b) hydroxy,
   (c) $C_{1-10}$ alkoxy,
   (d) $C_{1-5}$ alkoxycarbonyl,
   (e) $C_{1-5}$ alkylacyloxy,
   (f) phenylacyloxy,
   (g) phenoxycarbonyl,
   (h) phenyl $C_{1-5}$ alkylacyloxy,
   (i) phenyl $C_{1-5}$ alkoxy,
   (j) amino,
   (k) $C_{1-5}$ alkylamino,
   (l) di($C_{1-5}$ alkyl)amino,
   (m) phenylamino,
   (n) substituted phenylamino in which the substituents are X and Y,
   (o) phenyl $C_{1-5}$ alkylamino
   (p) substituted phenyl $C_{1-5}$ alkylamino in which the substituents are X and Y,
   (q) $C_{3-8}$ cycloalkyl,
   (r) phenyl,
   (s) substituted phenyl in which the substituents are X and Y,
   (t) phenylS(O)$_n$,
   (u) substituted phenylS(O)$_n$ in which the substituents are X and Y,
   (v) phenyl $C_{1-5}$ alkyl S(O)$_n$,
   (w) $C_{1-5}$ alkyl S(O)$_n$, (x) phenylaminoacyloxy,
(y) $C_{1-5}$alkyl aminoacyloxy,
(z) $C_{1-5}$alkyl acylamino,
(aa) di(phenyl$C_{1-5}$alkyl)phosphonyl,
(bb) di($C_{1-5}$alkyl)phosphinyl,
(5) $R_4$ together with the carbon atom to which it is attached represents a $C_{5-6}$ carbocyclic ring;
X and Y are independently selected from
a) OH;
b) halogen,
c) trifluoromethyl,
d) $C_{1-3}$alkoxy,
e) $C_{1-3}$alkyl carbonyloxy,
f) phenylcarbonyloxy,
g) $C_{1-3}$alkoxy carbonyl,
h) phenyloxycarbonyl,
i) hydrogen,
j) $C_{1-5}$alkyl;
halogen is Cl or F; n is 0, 1 or 2; a and b are double bonds, or one of a and b is a double bond, or both a and b are single bonds; or a pharmaceutically acceptable salt thereof.

2. A compound of claim 1 wherein:
$R_1$ is selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y, and
(i) oxo;
(3) $C_{3-8}$ cycloalkyl;
(4) substituted $C_{3-8}$ cycloalkyl in which one substituent is selected from
(a) $C_{1-10}$ alkyl,
(b) substituted $C_{1-10}$ alkyl in which the substituent is selected from
(i) halogen,
(ii) hydroxy,
(iii) $C_{1-10}$ alkoxy
(iv) $C_{1-5}$ acyloxy,
(v) $C_{1-5}$ alkoxycarbonyl,
(vi) phenyl,
(vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y;
$R_2$ and $R_3$ are each independently selected from the group consisting of:
(1) H;
(2) $R_6$;
$R_6$ is selected from
(1) substituted $C_{1-10}$ alkyl in which one or two substituent(s) is selected from
(a) amino;
(b) phenylacyloxy,
(c) phenoxycarbonyl;
(d) phenyl$C_{1-5}$alkylacyloxy,
(e) phenyl$C_{1-5}$alkoxy,
(f) $C_{1-5}$alkylamino,
(g) di($C_{1-5}$alkyl)amino,
(h) phenylamino,
(i) substituted phenylamino in which the substituents are X and Y,
(j) phenyl $C_{1-5}$alkylamino,
(k) substituted phenyl $C_{1-5}$alkylamino in which the substituents are X and Y,
(l) substituted phenyl in which the substituents are X and Y,
(m) phenylS(O)$_n$,
(n) substituted phenylS(O)$_n$ in which the substituents are X and Y,
(o) phenyl $C_{1-5}$ alkyl S(O)$_n$,
(p) $C_{1-5}$ alkylS(O)$_n$,
(q) phenylaminoacyloxy,
(r) $C_{1-5}$alkylaminoacyloxy,
(s) $C_{1-5}$alkylacylamino,
(t) di(phenyl$C_{1-5}$alkyl)phosphonyl,
(u) di($C_{1-5}$alkyl)phosphinyl,
(v) $C_{1-5}$alkyl-carbonyl-,
(w) carboxy-;
(2) 1(S)-hydroxyethyl;
(3) 1(S)-hydroxybenzyl;
provided that both of $R_2$ and $R_3$ are not H;
$R_4$ is:
(1) hydrogen;
(2) hydroxy,
(3) $C_{1-10}$ alkyl;
(4) substituted $C_{1-10}$ alkyl in which one or more substituents is selected from:
(a) halogen,
(b) hydroxy,
(c) amino;
(5) CH$_2$R$_{12}$ in which R$_{12}$ is selected from:
(a) $C_{1-5}$ alkoxy,
(b) $C_{1-5}$ alkoxy carbonyl,
(c) $C_{1-5}$ alkylacyloxy,
(d) phenylacyloxy,
(e) phenoxycarbonyl,
(f) phenyl$C_{1-5}$alkyl,
(g) phenyl$C_{1-5}$alkoxy
(h) $C_{1-5}$alkylamino,
(i) di($C_{1-5}$alkyl)amino,
(j) phenylamino,
(k) substituted phenylamino in which the substituents are X and Y,
(l) phenyl $C_{1-5}$alkylamino,
(m) substituted phenyl $C_{1-5}$ alkyl amino in which the substituents are X and Y,
(n) $C_{3-8}$ cycloalkyl,
(o) phenyl,
(p) substituted phenyl in which the substituents are X and Y,
(q) phenylS(O)$_n$,
(r) substituted phenylS(O)$_n$ in which the substituents are X and Y,
(s) phenyl $C_{1-5}$ alkylS(O)$_n$, (t) $C_{1-5}$ alkylS(O)$_n$,
(u) phenylaminoacyloxy,
(v) $C_{1-5}$ alkylaminoacyloxy,
(w) $C_{1-5}$ alkycylamino,
(x) di(phenyl$C_{1-5}$alkyl)phosphonyl,
(y) di($C_{1-5}$alkyl)phosphinyl;
(6) $R_4$ together with the carbon atom to which it is attached represents a cyclopropane ring;

X and Y are independently selected from:
a) OH,
b) F,
c) trifluoromethyl,
d) $C_{1-3}$alkoxy,
e) hydrogen,
f) $C_{1-5}$alkyl.

3. A compound of claim 2 wherein:
$R_1$ is $C_{1-10}$alkyl;
$R_4$ is H, CH$_3$, CH$_2$OH, or OH.

4. A compound of claim 3 wherein one of $R_2$ or $R_3$ is H, and one of $R_2$ or $R_3$ is $R_6$.

5. A compound of claim 4 wherein:
$R_6$ is
(a) substituted $C_{1-10}$alkyl in which one or two substituents are selected from:
(1) amino,
(2) $C_{1-5}$ alkylcarbonyl,
(3) $C_{1-5}$ alkylacyloxy,
(4) carboxy; or
(b) 1(S)-hydroxyethyl.

6. A compound of claim 5 wherein: $R_1$ is 2-butyl or 2-methyl-2-butyl; $R_4$ is CH$_3$.

7. A hypocholesterolemic, hypolipidemic pharmaceutical composition comprising a pharmaceutically acceptable carrier and a therapeutically effective amount of a compound as defined in claim 1.

8. A method of treating hypercholesterolemia in a subject in need of such treatment which comprises the administration of an antihypercholesterolemic effective amount of a compound of claim 1.

9. A method of inhibiting cholesterol biosynthesis in a subject in need of such treatment which comprises the administration of an antihypercholesterolemic effective amount of a compound of claim 1.

10. A compound of claim 6 selected from the group consisting of:
(1) 6(R)-(2-(8(R)-(2,2-dimethylbutyryloxy)-2(S)-methyl-6(S)-methyl-7(S)-(1(S)-hydroxy-ethyl)-1,2,6,7,8-8a(R)-hexahydronaphthyl)-1(S)-ethyl)-4-(R)-hydroxy-3,4,5,6-tetrahydro-2H-pyran-2-one;
(2) 6(R)-(2-(8(R)-2-methylbutyryloxy)-2(S)-methyl-6(S)-methyl-7(S)-(1(S)-hydroxyethyl)-1,2,-6,7,-8,8a(R)-hexahydronaphthyl)-1(S)-ethyl)-4(R)-hydroxy-3,4,5,6-tetrahydro-2H-pyran-2-one;
(3) 6(R)-(2-(8(R)-(2,2-dimethylbutylryloxy)-2(S)-methyl-6(S)-methyl-7(S)-(1(S)-hydroxybenzyl)-1,2,6,7,8,8a(R)-hexahydronaphthyl)-1(S)-ethyl)-4(R)-hydroxy-3,4,5,6-tetrahydro-2H-pyran-2-one;
(4) 6(R)-(2-(8(R)-(2-methylbutyryloxy)-2(S)-methyl-6(S)-methyl-7(S)-(1(S)-hydroxybenzyl)-1,2,6,7,8,8a(R)-hexahydronaphthyl)-1(S)-ethyl)-4(R)-hydroxy-3,4,5,6-tetrahydro-2H-pyran-2-one; and the corresponding esters.

* * * * *